United States Patent
Xu et al.

(10) Patent No.: US 7,732,199 B2
(45) Date of Patent: *Jun. 8, 2010

(54) PROCESS FOR MAKING TRANSPLANTABLE CARDIOMYOCYTES FROM HUMAN EMBRYONIC STEM CELLS

(75) Inventors: Chunhui Xu, Palo Alto, CA (US); Joseph D. Gold, San Francisco, CA (US)

(73) Assignee: Geron Corporation, Menlo Park, CA (US)

( * ) Notice: Subject to any disclaimer, the term of this patent is extended or adjusted under 35 U.S.C. 154(b) by 209 days.

This patent is subject to a terminal disclaimer.

(21) Appl. No.: 10/805,099

(22) Filed: Mar. 19, 2004

(65) Prior Publication Data

US 2005/0054092 A1    Mar. 10, 2005

Related U.S. Application Data

(63) Continuation-in-part of application No. 10/193,884, filed on Jul. 12, 2002, now Pat. No. 7,425,448.

(60) Provisional application No. 60/305,087, filed on Jul. 12, 2001, provisional application No. 60/322,695, filed on Sep. 10, 2001.

(51) Int. Cl.
C12N 5/08    (2006.01)

(52) U.S. Cl. .................................. 435/366; 435/404

(58) Field of Classification Search ................ 435/366, 435/404
See application file for complete search history.

(56) References Cited

U.S. PATENT DOCUMENTS

| | | | |
|---|---|---|---|
| 5,543,318 A | 8/1996 | Smith et al. | |
| 5,733,727 A | 3/1998 | Field | 435/6 |
| 5,843,780 A | 12/1998 | Thomson | 435/363 |
| 5,928,943 A | 7/1999 | Franz et al. | 435/363 |
| 6,015,671 A | 1/2000 | Field | 435/6 |
| 6,099,832 A | 8/2000 | Mickle et al. | 424/93.21 |
| 6,110,459 A | 8/2000 | Mickle et al. | 424/93.21 |
| 6,245,566 B1 | 6/2001 | Gearhart et al. | 435/384 |
| 6,261,836 B1 | 7/2001 | Cech et al. | 435/325 |
| 6,387,369 B1 | 5/2002 | Pittenger et al. | 424/93.7 |
| 6,399,300 B1 | 6/2002 | Field | 435/6 |
| 6,534,052 B1 | 3/2003 | Xiao et al. | 424/93.2 |
| 7,368,420 B1 | 5/2008 | Walsh | |
| 7,425,448 B2 | 9/2008 | Xu | |
| 7,452,718 B2 | 11/2008 | Gold et al. | |
| 2002/0061837 A1 | 5/2002 | Lough, Jr. et al. | |
| 2002/0142457 A1 | 10/2002 | Umezawa et al. | |
| 2002/0146678 A1 | 10/2002 | Benvenisty | |
| 2004/0005701 A1 | 1/2004 | Xu et al. | |
| 2004/0022367 A1 | 2/2004 | Talalai | |
| 2005/0037489 A1 | 2/2005 | Gepstein et al. | 435/366 |
| 2005/0054092 A1 | 3/2005 | Xu et al. | |
| 2005/0164382 A1 | 7/2005 | Xu | |
| 2005/0214938 A1 | 9/2005 | Xu et al. | |
| 2005/0227353 A1 | 10/2005 | Mummery | 435/366 |
| 2005/0266554 A1 | 12/2005 | D'Amour et al. | |
| 2009/0017465 A1 | 1/2009 | Xu | |
| 2009/0047739 A1 | 2/2009 | Xu et al. | |

FOREIGN PATENT DOCUMENTS

| | | |
|---|---|---|
| AU | 729377 | 2/2001 |
| WO | WO 92/13066 | 8/1992 |
| WO | WO 95/14079 | 5/1995 |
| WO | WO 99/49015 | 9/1999 |
| WO | WO 00/06701 | 2/2000 |
| WO | WO 00/70021 | 11/2000 |
| WO | WO 00/78119 | 12/2000 |
| WO | WO 01/22978 | 4/2001 |
| WO | WO 01/48151 | 7/2001 |
| WO | WO 01/048151 A1 | 7/2001 |
| WO | WO 01/51616 | 7/2001 |
| WO | WO 01/53465 | 7/2001 |
| WO | WO 01/68814 | 9/2001 |
| WO | WO 02/09650 | 2/2002 |
| WO | WO 02/13760 | 2/2002 |
| WO | WO 02/19893 | 3/2002 |
| WO | WO 02/30206 | 4/2002 |
| WO | WO 02/083864 A2 | 10/2002 |
| WO | WO 03/006950 | 1/2003 |
| WO | WO 2004/081205 | 9/2004 |

OTHER PUBLICATIONS

Murrell, WG et al. Mech Ageing Dev 77(2):abstract, 1994.*
Verfaillie, CM. et al. Hematotlogy 2002:369-391, 2002.*
Takahshi, K et al. J Cardiovasc Pharm 41(5):726-0733, 2003.*
Nair, P and RP Nair. Indian J Exp Biol 35(5):abstract, 1997.*
Pandur, P. Biol Cell 97:197-210, 2005.*
Schuldiner, M et al. PNAS 97(21):11307-11312, 2000.*
Lim, J. & Bodnar, A., "Proteome analysis of conditioned medium from mouse embryonic fibroblast feeder layers which support the growth of human embryonic stem cells," Proteomics 2:1187-203 (2002).
Khamsi, R., "Market Watch," Nature 437:1231 (2005).

(Continued)

Primary Examiner—Thaian N Ton
Assistant Examiner—Marcia S Noble
(74) Attorney, Agent, or Firm—E. Stewart Mittler

(57) ABSTRACT

This invention provides populations human cells of the cardiomyocyte lineage. The cells are obtained by causing cultures of pluripotent stem cells to differentiate in vitro, and then harvesting cells with certain phenotypic features. Differentiated cells bear cell surface and morphologic markers characteristic of cardiomyocytes, and a proportion of them undergo spontaneous periodic contraction. Highly enriched populations of cardiomyocytes and their replicating precursors can be obtained, suitable for use in a variety of applications, such as drug screening and therapy for cardiac disease.

8 Claims, 14 Drawing Sheets

OTHER PUBLICATIONS

Figure 1:
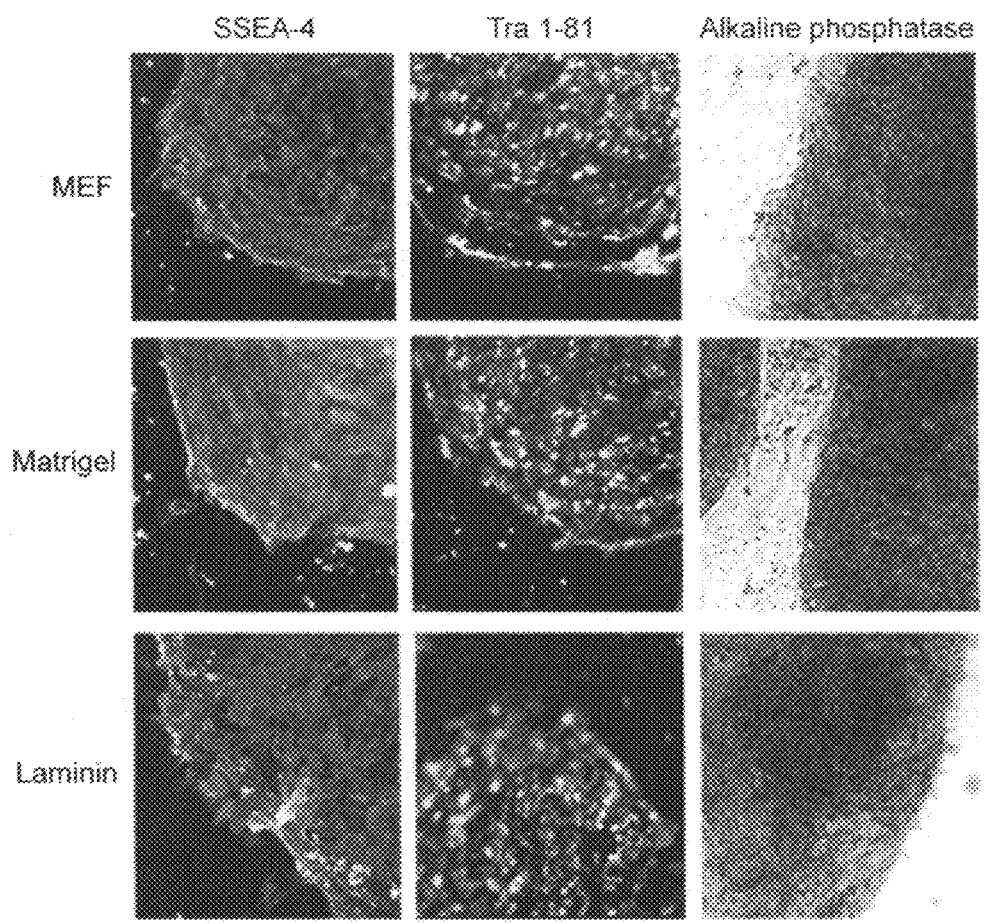

Murry, C. et al., "Muscle cell grafting for the treatment and prevention of heart failure," *J. Cardiac Failure* 8(6):S532-S541 (2002).

Rice, N. & Leinwand, L., "Skeletal myosin heavy chain function in cultured lung myofibroblasts," *J. Cell Biol.* 163(1):119-29 (2003).

Shamblott, M. et al., "Human embryonic germ cell derivatives express a broad range of developmentally distinct markers and proliferate extensively in vitro," *Proc, Natl. Acad. Sci. USA* 98(1):113-8 (2001).

Thomson, J. et al., "Isolation of a primate embryonic stem cell line," *Proc. Natl. Acad. Sci. USA* 92:7844-8 (1995).

Caspi, O. & Gepstein, L., "Potential applications of human embryonic stem cell-derived cardiomyocytes," *Ann. N. Y. Acad. Sci.* 1015:285-98 (2004).

Charron, F. & Nemer, M., "GATA transcription factors and cardiac development," *Semin. Cell Dev. Biol.* 10(1):85-91 (1999).

Goh, G. et al., "Molecular and phenotypic analysis of human embryonic stem cell-derived cardiomyocytes," *Thromb. Haemost.* 94:728-37 (2005).

Khamsi, R. "Geneticists Hail Variety Show, Map of DNA Differences will Help Experts Tailor Drugs," *Nature*, online, 2 pages (Oct. 26, 2005).

Laflamme, M. et al., "Formation of human myocardium in the rat heart from human embryonic stem cells," *Am. J. Pathol.* 167(3):663-71 (2005).

Strauer, B. et al., "Stem Cell Therapy in Perspective," *Circulation* 107:929-34 (2003).

Van Laake, L. et al., "Cardiomyocytes derived from stem cells," *Ann. Med.* 37:499-512 (2005).

Xiao, Y-F. et al., "Cardiac application of embryonic stem cells," *Acta Physiologica Sinica* 55(5):493-504 (2003).

Xu, C. et al., "Cardiac Bodies: A novel culture method for enrichment of cardiomyocytes derived from human embryonic stem cells," *Stem Cells Dev.* 15:631-9 (2006).

Czyz, J. et al., "Potential of embryonic and adult stem cells in vitro," *Biol. Chem.* 384:1391-409 (2003).

Gerecht-Nir, S. et al., "Vascular gene expression and phenotypic correlation during differentiation of human embryonic stem cells," *Dev. Dyn.* 232:487-97 (2005).

Oh, S. et al., "Human embryonic stem cells: technological challenges towards therapy," *Clin. Exp. Pharmacol. Physiol.* 33:489-95 (2006).

"Alpha-1 adrenergic receptor," Wikipedia entry, 4 pages, printed Mar. 26, 2009.

"Isoprenaline," Wikipedia entry, 2 pages, printed Mar. 25, 2009.

Boheler, K. et al., "Differentiation of pluripotent embryonic stem cells into cardiomyocytes," *Circ. Res.* 91:189-201 (2002).

Cerbai, E. et al. "Electrophysiologic effects of lercanidipine on repolarizing potassium currents," *J. Cardiovasc. Pharmacol.* 36:584-91 (2000).

Corsini, A. et al. "Effect of the new calcium antagonist lercanidipine and its enantiomers on the migration and proliferation of arterial myocytes," *J. Cardiovasc. Pharmacol.* 28:687-94 (1996).

De Pater, E. et al. "Distinct phases of cardiomyocyte differentiation regulate growth of the zebrafish heart," *Development* 136:1633-41(2009).

Feng, J. et al. "Antisense oligodeoxynucleotides direccted against Kv1.5 mRNA specifically inhibit ultrarapid delayed rectifier K+ current in cultured adult human atrial myocytes," *Circ. Res.* 80:572-9 (1997).

Goldman, B. et al., "Epidermal growth factor promotes a cardiomyoblastic phenotype in human fetal cardiac myocytes," *Exp. Cell Res.* 228:237-45 (1996).

Piao, S. et al., "A simplified method for identification of human cardiac myosin heavy-chain isoforms," *Biotechnol. Appl. Biochem.* 37:27-30 (2003).

Tweedie, D. et al. "The effect of alterations to action potential duration on Beta-adrenoceptor-mediated aftercontractions in human and guinea-pig ventricular myocytes," *J. Mol. Cell Cardiol.* 29:1457-67 (1997).

Alsan et al., Regulation of avian cardiogenesis by Fgf8 signaling, Development, 129:1935 (2002).

Andree et al., BMP-2 induces expression of cardiac lineage markers and interferes with somite formation in chicken embryos, Mech. of Deve., 70:119 (1998).

Antin et al., Regulation of avian precardiac mesoderm development by insulin and insulin-like growth factors, J. Cell. Physiol. 168:42 (1996).

Arai et al., Murine cardiac progenitor cells require visceral embryonic endoderm and primitive streak for terminal differentiation, Dev. Dynamics 210:344 (1997).

Barron et al., Repuirement for BMP and FGF signaling during cardiogenic induction in non-precrdiac mesoderm is specific, transient, and cooperative, Dev. Dynamics 218:383 (2000).

Bauwens et al., Development of perfusion fed bioreactor for embryonic stem cell-derived cardiomyocyte generation: oxygen-mediated enhancement of cardiomyocyte output, biotechnology and bioengineering 90 (4):452 (2005).

Behfar et al., Stem cell differentiation requires a paracrine pathway in the heart, FASEB J, 16:1558 (2002).

Claycomb et al., HL-1 cells: A cardiac muscle cell line that contracts and retains phenotypic characteristics of the adult cardiomyocyte, Proc. Natl. Acad. Sci. USA 95:2979(1998).

Dang et al. Controlled, scalable embryonic stem cell differentiation culture, Stem Cells, 22:275 (2004).

Doevendans et al., Differentiation of cardiomyocytes in floating embryoid bodies is comparable to fetal cardiomyocytes, J. Mol. Cell Cardiol, 32:839 (2000).

Dubus et al., Contractile protein gene expression in serum-free cultured adult rat cardiac myocytes, Pflugers Arch, 423:455 (1993).

Fukuda, Development of regenerative cardiomyocytes from mesenchymal stem cells for cardiovascular tissue engineering, Artificial Organs 25:187 (2001).

Gepstein, Derivation and Potential Applications of Human Embronic Stem Cells, Circulation Research, 91 (10):866 (2002).

Grepin et al., Enhanced cardiogenesis in embryonic stem cells overexpressing the GATA-4 transcription factor, Development 124:2387 (1997).

Gryschenko et al., Outwards currents in embryonic stem cell-derived cardiomyocytes, Pflugers Arch. 439:798 (2000).

Heng et al., Strategies for directing the differentiaion of stem cells into the cardiomyogenic lineage in vitro, Cardiovascular Research, 62:34 (2004).

Itskovitz-Eldor et al., Differentiation of Human Embronic Stem Cells into Embryoid Bodies Comprising the Three Emryonic Germ Layers, Mol. Med. 6:88 (2000).

Johansson et al., Evidence for involvement of activin A and bone morphogenetic protein 4 mammalian mesoderm and hematopoietic development, Mollecular and Cellular Biology, 15(1):141 (1995).

Kawai et al., Efficient cardiomyogenic differentiation of embryonic stem cell by fibroblast growth factor 2 and bone morphogenetic protein 2, Circ J 68:691 (2004).

Kehat e al., Electromechanical integration of cardiomyocytes derived from human embryonic stem cells, Nature Biotechnology, 22(10):1282 (2004).

Kehat et al., Abstract, Human embryonic stem cells can diffrentiate into cyocytes with structural and functional properties of cardiomyocytes, J. Clin. Invest., 108:407 (2001).

Kehat et al., Long term high-resolution, Electrophysiological assessment of human embryonic stem cell derived cardiomyocytes: A novel in vitro model for the human heart, Circulation, 102(18 Suppl. II):11-4 (2000).

Kessler et al., Myoblast cell grafting into heart muscle: Cellular biology and potential applications, Annu. Rev. Physiol. 61:219(1999).

Klug et al. Genetically selected cardiomyocytes from differentiating embryonic stem cells form stable intracardiac grafts, J. Clin. Invest. 98:216 (1996).

Koide et al., Atrial natriuretic peptide accelerates proliferation of chick embryonic cardiomyocytes in vitro, Differentiation 61:1 (1996).

Kolossov et al., Functional characteristics of ES cell-derived cardiac precursor cells identified by tissue-specific expression of the green fluorescent protein, J. Cell Biol. 143:2045 (1998).

Ladd et al., Regulation of avian cardiac myogenesis by activin/TGFB and bone morphogenetic proteins, Dev. Biology 204:407 (1998).

Lev et al., Differentiation pathways in human embryonic stem cell-derived cardiomyocytes, Ann. N.Y. Acad. Sci. 1047:50 (2005).

Liechty et al., Human mesenchymal stem cells engraft and demonstrate site-specific differentiation after in utero transplantation in sheep, Nature Med. 6:1282 (2000).

Li et al., Isolation of cardiomyocytes from human myocardium for primary cell culturing, J. Tiss. Cult. Meth. 15:147 (1993).

Lough et al., Combined BMP-2 and FGF-4, but neither factor alone, induces cardiogenesis in non-precardiac embryonic mesoderm, Dev. Biology 178:198 (1996).

Makino et al., Cardiomyocytes can be generated from marrow stromal cells in vitro, J. Clin. Invest. 103:697 (1999).

Maltsev et al., Embryonic stem cells differentiate in vitro into cardiomyocytes representing sinusnodal, atrial and ventricular cell types, Mechanisms Dev. 44:41 (1993).

Matsushita et al., Formation of cell junctions between grafted and host cardiomyocytes at the border zone of rat myocardial infraction, Circulation 100[suppl. II]:II-262 (1999).

Marvin et al., Inhibition of Wnt activity induces heart formation from posterior mesoderm, Genes Dev. 15:316 (2001).

McBurney et al., Control of muscle and neuronal differentiation in a cultured embryonal carcinoma cell line, Nature 299:165 (1982).

McDowell et al., Activin as a morphogen in *Xenopus mesoderm* induction, Seminars in Cell & Development Biology, 10:311 (1999).

Menard et al., Transplantation of cardiac-committed mouse embryonic stem cells to infarcted sheep myocardium: preclinical study, Lancet 366:1005 (2005).

Messina et al., Isolation and expansion of adult ardiac stem cells from human and murine heart, 95:911 (2004).

Min et al., Transplantation of embryonic stem cells improves cardiac function in postinfacted rats, J. Appl. Physiol. 92:288 (2002).

Monzen et al., Bone morphogenetic proteins induce cardiomyocyte differentiation through the mitogen-activated protein kinase kinase kinase kinase TAK1 and cardiac transcription factors CsxNkx-2.5 and GATA-4, Mol. Cell Biol. 19:7096 (1999).

Muller et al., Selection of ventricular-like cardiomyocytes from ES cells in vitro, FASEB J. 14:2540 (2000).

Mummery et al., Cardiomyocyte differentiation of mouse and human embryonic stem cells, J Anat., 200 (Pt 3):233-242, 2002.

Mummery et al., Differentiation of human embryonic stem cells to cardiomyocytes: Role of coculture with visceral endoderm-like cells, Circulation, 107:2733(2003).

Muslin et al., Wll-defined growth factors promote cardiac development in axoloti mesodermal explants, Development 112:1095 (1991).

Narita et al., Cardiomyocyte differentiation by GATA-4-deficient embryonic stem cells, Development 124:3755 (1997).

Olson et al., Molecular pathways controlling heart development, Science 272:671 (1996).

Odorico et al., Multilineage differntiation from human embryonic stem cell lines, Stem Cells, 19:193 (2001).

Oh et al. Cardiac progenitor cells from adult myocardium: Homing, differentiation, and fusion after infarction, PNAS 100(21): 12313 (2003).

O'Shea, Embryonic Stem cell models of development, Anatomical Record, 257 (1):32 (1999).

Qin et al., Gene transfer of transforming growth factor-B1 prolongs murine cardiac allograft survival by inhibiting cell-mediated immunity, Human Gene Therapy 7:1981 (1996).

Reubinoff et al., Embryonic stem cell line from human blastocysts: somatic differentiation in vitro, Nature Biotech. 18:399 (2000).

Satin et al.,Mechanism of spontaneous excitability in human embryonic stem cell derived cardiomyocytes, J Physiol 559(2):479 (2004).

Scalia et al., Regulation of the Akt/Glycogen synthase kinase-3 axis by insulin-like growth factor-II via activation of the human insulin receptor isoform-A, J. Cell. Biochem. 82:610 (2001).

Schlange et al., BMP2 is required for early heart development during a distinct time period, Mechanisms of Development, 91:259 (2000).

Schneider et al., Wnt antagonism initiates cardiogenesis in *Xenopus laevis*, Genes Dev. 15:304 (2001).

Schuldiner et al., Effects of eight growth factors on the differentiation of cells derived from human embryonic stem cells, PNAS 97:11307 (2000).

Schultheiss et al., Induction of avian cardiac myogenesis by anterior endoderm, Development 121:4203 (1995).

Schultheiss et al., A role for bone morphogenetic proteins in the induction of cardiac myogenesis, Genes & Dev. 11:451 (1997).

Shamblott et al., Derivation of pluripotent stem cells from cultured human primordial germ cells, Proc. Natl. Acad. Sci. USA 95:13726 (1998).

Shi et al., BMP signaling is required for heart formation in vertebrates, Dev. Biol. 224:226 (2000).

Skerjane, et al., Myocyte enhancer factor 2C and Nkx2-5 up-regulate each other's expression and initiate cardiomygenesis in P19 cells, J. Biol. Chem. 273:34904 (1998).

Sugi et al., Activin-A and FGF-2 mimic the inductive effects of anterior endoderm on terminal cardiac myogenesis in vitro, Dev. Biology 168:567 (1995).

Symes et al., Morphological differences in Xenopus embryonic mesodermal cells are specified as and early response to distinct threshold concentrations of activin, Development 120:2339 (1994).

Thomson et al., Embryonic stem cell lines derived from human blastocysts, Science 282:1145 (1998).

Velez et al., Modulationo f contractile protein troponin-T in chick myocardial cells by basic fibroblast growth factor and platelet-derived growth factor during development, J. Cardiovascular Pharmacology 24:906 (1994).

Volz et al., Longevity of adult ventricular rat heart muscle cells in serum-free primary culture, J. Mol. Cll Cardiol. 23:161 (1991).

Walters et al., Bone morphogenetic protein function is required for terminal differentiation of the heart but not for early expression of cardiac marker genes, Mechanisms of Development, 100:263 (2001).

Wobus et al., In vitro cellular models for cardiac development and pharmacotoxicolgy, Toxic. in Vitro 9:477 (1995).

Wobus et al., Development of cardiomyocytes expressing cardiac-specific genes, action potentials, and ionic channels during embryonic stem cell-derived cardiogenesis, Ann. N.Y. Acad. Sci. 752:460 (1995).

Wobus et al., Retinoic acid accelerates embryonic stem cell-derived cardiac differentiation and enhances development of ventricular cardiomyocytes, J. Mol. Cell Cardiol. 29:1525 (1997).

Xu et al., Feeder-free growth of undifferentiated human embryonic stem cells, 19 (10): 971 (2001).

Xu et al., Characterization and enrichment of cardiomyocytes derived from human embryonic stem cells, Circulation Research, 91 (6): 501 (2002).

Xu et al., Specific arrest of cardiogenesis in cultured embryonic stem cells lacking Cripto-1, Dev Biol. 196:237 (1998).

Yatskievych et al., Induction of cardiac myogenesis in avian pregastrula epiblast: the role of the hypoblast and activin, Development, 124:2561 (1997).

Zandstra et al., Scalable production of embryonic stem cell-derived cardiomyocytes, Tissue Engineering, 9(4):767 (2003).

Zhu et al., Evidence that fibroblast growth factors 1 and 4 participate in regulation of cardiogenesis, Dev. Dynamics 207:429 (1996).

Zingg et al., Genetic and epigenetic aspects of DNA methylation on genome expression, evolution, mutation and carcinogenesis, Carcinogenesis 18:869 (1997).

Goldman, B. et al., "Human fetal cardiocytes in enriched culture," *In vitro Cell. Dev. Biol. Animal* 31:731-4 (1995).

* cited by examiner

PROCESS FOR MAKING TRANSPLANTABLE CARDIOMYOCYTES FROM HUMAN EMBRYONIC STEM CELLS

REFERENCE TO RELATED APPLICATIONS

This application is a continuation-in-part of U.S. utility application Ser. No. 10/193,884, filed Jul. 12, 2002, now U.S. Pat. No. 7,425,448; and claims the priority benefit of U.S. provisional applications 60/305,087, filed Jul. 12, 2001; and 60/322,695, filed Sep. 10, 2001.

The priority documents are hereby incorporated herein by reference in its entirety, along with International Patent Publications WO 01/51616; and WO 03/020920, with respect to the culturing and genetic alteration of pPS cells, differentiation into cardiomyocyte lineage cells, and use of the differentiated cells.

BACKGROUND

Heart disease is one of the most serious health concerns in the western world. It is estimated that 61 million Americans (nearly 1 in 5 men and women) have one or more types of cardiovascular disease (National Health and Nutrition Examination Survey III, 1988-94, Center of Disease Control and the American Heart Association). Widespread conditions include coronary heart disease (12.4 million), congenital cardiovascular defects (1 million), and congestive heart failure (4.7 million). A central challenge for research in regenerative medicine is to develop cell compositions that can help reconstitute cardiac function in these conditions.

Most of the research work done so far has been performed using stem cells of various kinds developed using rodent animal models.

Maltsev, Wobus et al. (Mechanisms Dev. 44:41, 1993) reported that embryonic stem (ES) cells from mice differentiated in vitro via embryo-like aggregates into spontaneously beating cardiomyocytes. Wobus et al. (Ann. N.Y. Acad. Sci. 27:460, 1995) reported that pluripotent mouse ES cells reproduce cardiomyocyte development from uncommitted embryonal cells to specialized cellular phenotypes of the myocardium. Embryoid bodies were plated, cultured, dissociated, and assayed by immunofluorescence and electrophysiological studies. The cells were reported to express cardiac-specific genes and all major heart-specific ion channels. Wobus et al. (J. Mol. Cell Cardiol. 29:1525, 1997) reported that retinoic acid accelerates ES cell-derived cardiac differentiation and enhances development of ventricular cardiomyocytes. The investigation used cell clones transfected to express β-galactosidase under control of the MLC-2v promoter.

Kolossov et al. (J. Cell Biol. 143:2045, 1998) reported isolation of cardiac precursor cells from mouse ES cells using a vector containing green fluorescent protein under control of the cardiac α-actin promoter. Patch clamp and $Ca^{++}$ imaging suggested expression of L-type calcium channels starting from day 7 of embryoid body development. Narita et al. (Development 122:3755, 1996) reported cardiomyocyte differentiation by GATA-4 deficient mouse ES cells. In chimeric mice, GATA-4 deficient cells were found in endocardium, myocardium and epicardium. The authors proposed that other GATA proteins might compensate for lack of GATA-4.

U.S. Pat. No. 6,015,671 (Field) and Klug et al. (J. Clin. Invest. 98:216, 1996) reported that genetically selected cardiomyocytes from differentiating mouse ES cells form stable intracardiac grafts. Cells were selected from differentiating murine ES cells using the α-cardiac myosin heavy chain (MHC) promoter driving aminoglycoside phosphotransferase or $neo^r$, and selecting using the antibiotic G418. Following transplantation into the hearts of adult dystrophic mice, labeled cardiomyocytes were reportedly found as long as 7 weeks after transplantation. International patent publication WO 00/78119 (Field et al.) proposes a method for increasing proliferative potential of a cardiomyocyte by increasing the level of cyclin D2 activity.

Doevendans et al. (J. Mol Cell Cardiol. 32:839, 2000) proposed that differentiation of cardiomyocytes in floating embryoid bodies is comparable to fetal cardiomyocytes. Rodent stem cell derived cardiomyocytes were reported to differentiate into ventricular myocytes having sodium, calcium, and potassium currents.

Muller et al. (FASEB J. 14:2540, 2000) reported the isolation of ventricular-like cardiomyocytes from mouse ES cells transfected with green fluorescent protein under control of the ventricular-specific 2.1 kb myosin light chain-2v promoter and the CMV enhancer. Electrophysiological studies suggested the presence of ventricular phenotypes, but no pacemaker-like cardiomyocytes. Gryschenko et al. (Pflugers Arch. 439:798, 2000) investigated outward currents in mouse ES cell derived cardiomyocytes. The predominant repolarizing current in early-stage ES-derived cardiomyocytes was 4-aminopyridine sensitive transient outward current. The authors concluded that in early stage cardiomyocytes, this transient outward current plays an important role in controlling electrical activity.

International patent publication WO 92/13066 (Loyola University) reported the construction of rat myocyte cell lines from fetal material genetically altered with the oncogenes v-myc or v-ras. U.S. Pat. Nos. 6,099,832 and 6,110,459 (Mickle et al., Genzyme) report on the use of various combinations of adult cardiomyocytes, pediatric cardiomyocytes, fibroblasts, smooth muscle cells, endothelial cells, or skeletal myoblasts to improve cardiac function in a rat model. U.S. Pat. No. 5,919,449 (Diacrin) reports on the use of pig cardiomyocytes for treating cardiac insufficiency in a xenogeneic subject. The cells are obtained from an embryonic pig between ~20-30 days gestation.

Makino et al. (J. Clin. Invest. 103:697, 1999) and K. Fukuda (Artificial Organs 25:1878, 2001) developed regenerative cardiomyocytes from mesenchymal stem cells for cardiovascular tissue engineering. A cardiomyogenic cell line was developed from bone marrow stroma, and cultured for more than 4 months. To induce cell differentiation, cells were treated with 5-azacytidine for 24 hours, which caused 30% of the cells to form myotube-like structures, acquire cardiomyocyte markers, and begin beating.

Most established cardiomyocyte lines have been obtained from animal tissue. There are no established cardiomyocyte cell lines that are approved for widespread use in human cardiac therapy.

Liechty et al. (Nature Med. 6:1282, 2000) reported that human mesenchymal stem cells engraft and demonstrate site-specific differentiation after in utero transplantation into sheep. Long-term engraftment was reportedly achieved for as long as 13 months after transplantation, which is after the expected development of immunocompetence. International patent publication WO 01/22978 proposes a method for improving cardiac function in a patient with heart failure, comprising transplanting autologous bone marrow stroma cells into the myocardium to grow new muscle fibers.

International patent publication WO 99/49015 (Zymogenetics) proposes the isolation of a nonadherent pluripotent cardiac-derived human stem cell. Heart cells are suspended, centrifuged on a density gradient, cultured, and tested for cardiac-specific markers. Upon proliferation and differentiation, the claimed cell line produces progeny cells that are fibroblasts, muscle cells, cardiomyocytes, keratinocytes, osteoblasts, or chondrocytes.

It is unclear whether any of the cell preparations exemplified in these publications can be produced in sufficient quantities for mass marketing as a therapeutic composition for regenerating cardiac function.

A more promising source of regenerative cells for treating cardiac disease is human pluripotent stem cells obtained from embryonic tissue.

Thomson et al. (Proc. Natl. Acad. Sci. USA 92:7844, 1995) were the first to successfully culture embryonic stem cells from primates, using rhesus monkeys and marmosets as a model. They subsequently derived human embryonic stem (hES) cell lines from human blastocysts (Science 282:114, 1998). Gearhart and coworkers derived human embryonic germ (hEG) cell lines from fetal gonadal tissue (Shamblott et al., Proc. Natl. Acad. Sci. USA 95:13726, 1998). International Patent Publication WO 00/70021 refers to differentiated human embryoid cells, and a method for producing them from hES cells. International Patent Publication WO 01/53465 outlines the preparation of embryoid body-derived cells from hEG cells.

Both embryonic stem cells and embryonic germ cells can proliferate in vitro without differentiating, they retain a normal karyotype, and they retain the capacity to differentiate to produce a variety of adult cell types. However, it is clear that the propagation and differentiation of human pluripotent stem cells is subject to very different rules than what has been developed for the culture of rodent stem cells.

Geron Corporation has developed novel tissue culture environments that allow for continuous proliferation of human pluripotent stem cells in an environment essentially free of feeder cells. See Australian patent AU 729377, and International Patent Publication WO 01/51616. Being able to culture stem cells in a feeder-free environment provides a system in which cellular compositions can be readily produced that are in compliance with the regulatory requirements for human therapy.

In order to realize the potential of pluripotent stem cells in the management of human health and disease, it is now necessary to develop new paradigms to drive these cells into populations of therapeutically important tissue types.

SUMMARY

This invention provides a system for efficient production of primate cells that have differentiated from pluripotent cells into cells of the cardiomyocyte lineage.

One embodiment of this invention is a population comprising cells of the cardiomyocyte lineage. The cells have particular properties referred to in this disclosure. For example, they may:

be end-stage cardiomyocytes be cardiac precursors capable of proliferation in vitro and capable of differentiation in vitro or in vivo into cells having any of the aforelisted features express one or more of the following markers from an endogenous gene: cardiac troponin I (cTnI), cardiac troponin T (cTnT), atrial natriuretic factor (ANF), or myosin heavy chain (MHC).

express other phenotypic markers referred to in this disclosure be produced by differentiation of primate pluripotent stem (pPS) cells have the same genome as an established human embryonic stem (hES) cell line exhibit spontaneous periodic contractile activity express other characteristics of cardiomyocytes, such as ion channels or appropriate electrophysiology The cell populations of this invention may be enriched to the point where ~5, ~20, or ~60% of the cells have the characteristics referred to. If desired, the cells can also be genetically altered to extend replicative capacity with a telomerase reverse transcriptase, or to express a growth factor, cardiotropic factor, or transcription regulatory element.

Another embodiment of the invention is a method for producing such cell populations, comprising differentiating pPS cells or their progeny in a suitable growth environment. In an exemplary method, hES cells are cultured in an environment essentially free of feeder cells, and then caused to differentiate into cardiomyocytes or cardiomyocyte precursors bearing one or more of the features referred to above. In some circumstances, the differentiation method may involve one or more of the following: culturing the pPS cells in suspension culture to form embryoid bodies or cell aggregates, culturing in a growth environment comprising one or more cardiotropic factors, separating cells bearing cardiomyocyte markers or undergoing spontaneous contractions from other cells in the population by density separation or another suitable technique, and reculturing the separated cells to promote further expansion or enrichment.

Processing of the cell population can involve the formation of Cardiac Bodies™, which are clusters of cells in suspension, many of which undergo spontaneous contraction. In an exemplary method, pPS derived cell populations expressing characteristics of the cardiomyocyte lineage are suspended, and single cells are removed, leaving cells that are present as clusters. The clustered cells are then resuspended and recultured in fresh medium for a suitable period. The cells can be taken through multiple cycles of separating, resuspending, and reculturing, until a composition is obtained in which 80 to 100% of the cell clusters undergo spontaneous contraction. Accordingly, the invention embodies methods of manufacturing Cardiac Bodies™ from pPS cells and mixed populations of cardiomyocyte lineage cells, and compositions of the Cardiac Bodies™ themselves, optionally in the form of a cultured cell composition, or a composition suitable for administration to a mammalian subject.

A further embodiment of the invention is a method of screening a compound for an effect on cardiomyocytes. This involves combining the compound with the cell population of the invention, and then determining any modulatory effect resulting from the compound. This may include examination of the cells for toxicity, metabolic change, or an effect on contractile activity.

Another embodiment of the invention is a medicament or delivery device containing a cell population of this invention intended for treatment of a human or animal body. The cell population may be formulated as a medicament for treating a condition of the heart. A further embodiment of the invention is a method of reconstituting or supplementing contractile activity in cardiac tissue, comprising contacting the tissue with a cell population of this invention. Included is the treatment of a heart condition in an individual, in which the individual is administered a cell population of this invention in a suitable formulation.

These and other embodiments of the invention will be apparent from the description that follows. The compositions, methods, and techniques described in this disclosure hold considerable promise for use in diagnostic, drug screening, and therapeutic applications.

DRAWINGS

FIG. 1 shows marker expression detected by immunocytochemistry for undifferentiated human embryonic stem (hES) cells. The cultures were grown according to conventional methods on mouse embryonic feeder cells, or in a feeder-free environment comprising extracellular matrices Matrigel® or laminin in conditioned medium. hES cells grown in feeder-free culture have phenotypic markers similar to those of hES grown on a feeder layer of primary mouse fibroblasts.

Figure 2:
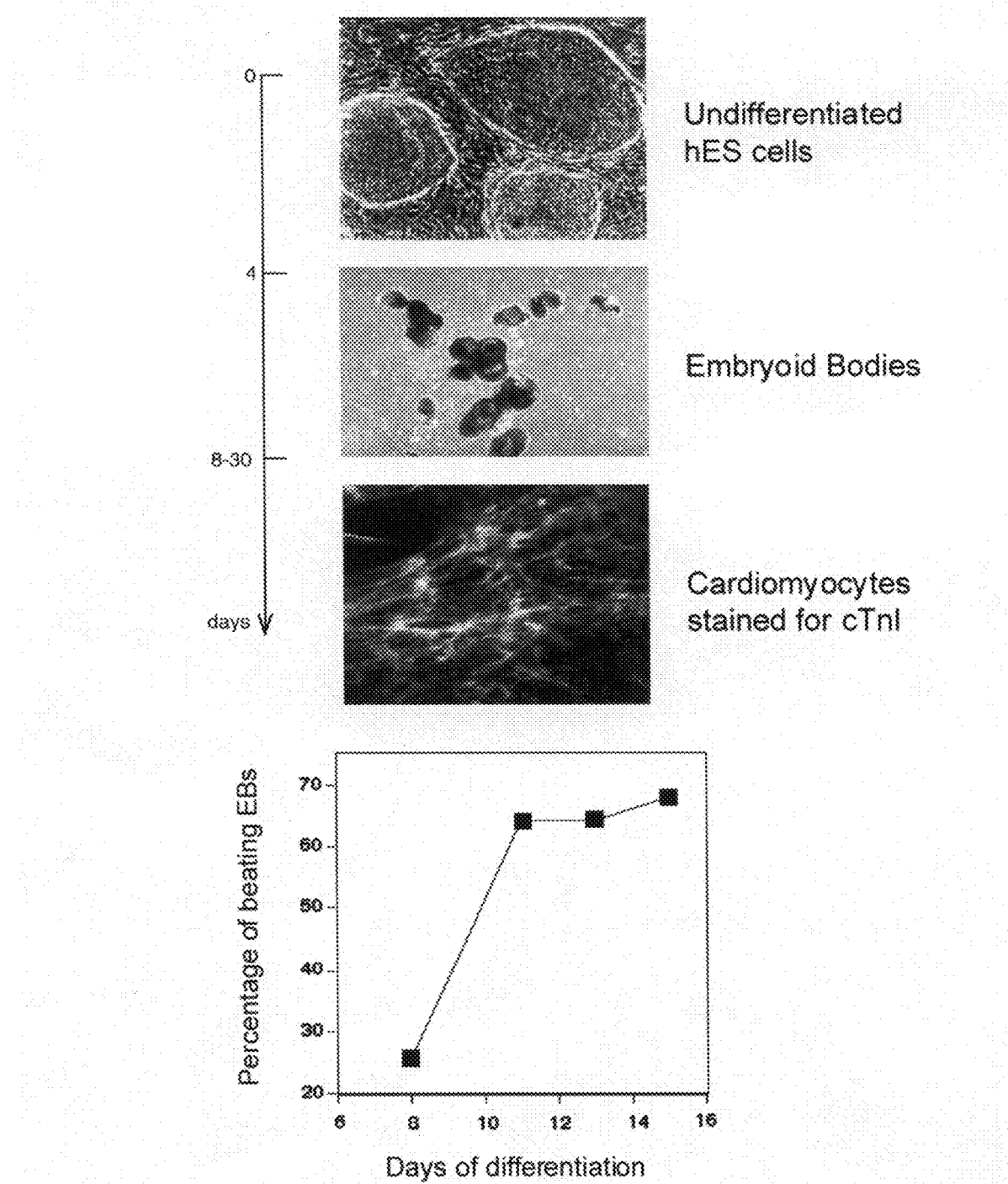

FIG. 2 is a scheme for obtaining cardiomyocytes from pPS cells (Upper Panel), and the kinetics of cardiomyocyte formation (Lower Panel). Example 2 provides an illustration in which differentiation was initiated by culturing hES cells in suspension to form embryoid bodies. After 4 days in suspension culture, embryoid bodies were transferred to gelatin-coated plates. Spontaneously contracting cells were observed in various regions of the culture at differentiation day 8, increasing in number over the next week until over 60% of the cell masses contained contracting cells.

Figure 3:
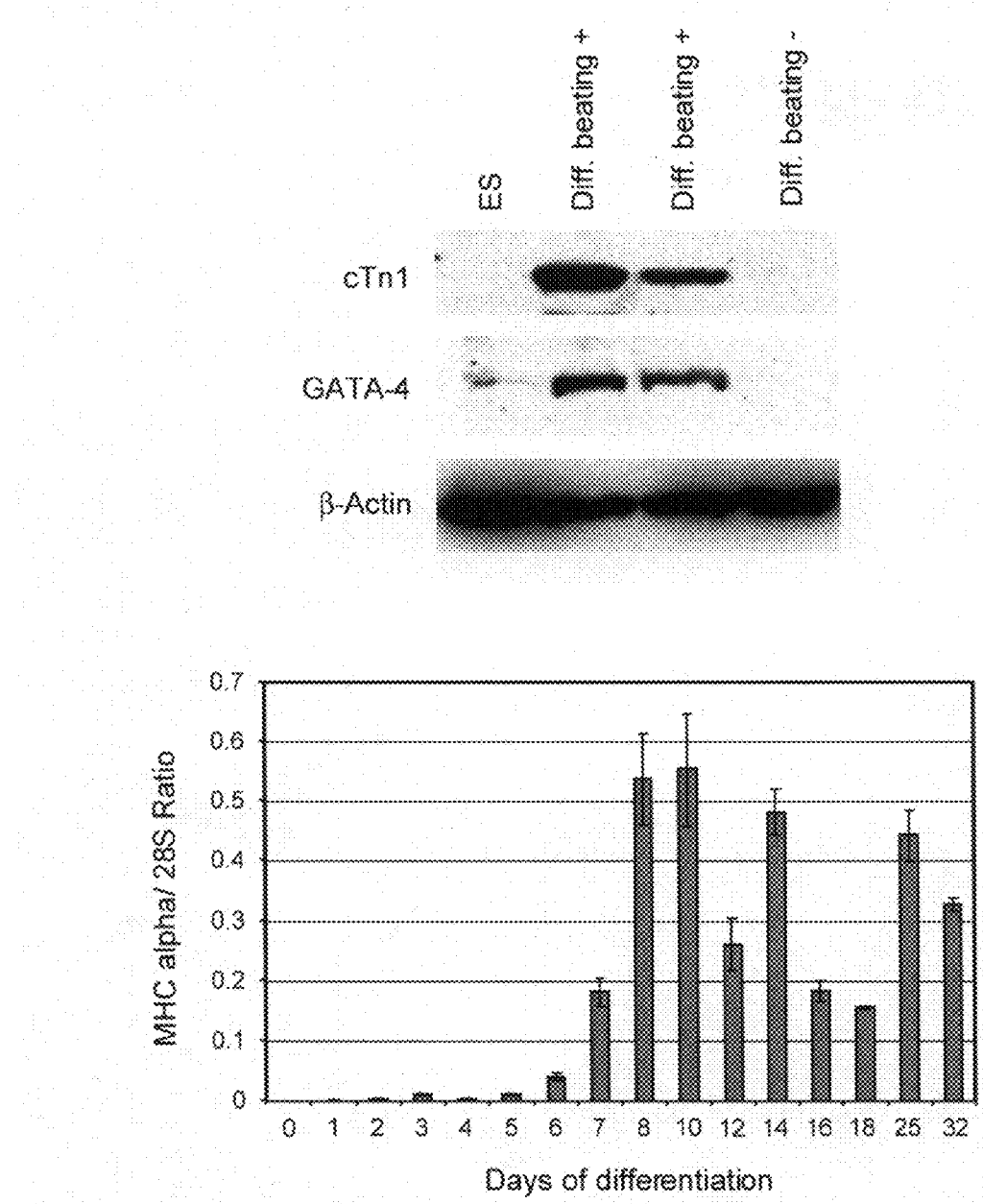

FIG. 3 shows markers detected in cardiomyocytes differentiated from human embryonic stem (hES) cells. The Upper Panel shows results of Western blot analysis for the markers cardiac troponin I (cTnI), GATA-4, and β-actin. cTnI and GATA-4 were observed in contracting cells, but not in other wells containing no contracting cells. The Lower Panel shows the kinetics of expression of α-cardiac myosin heavy chain (MHC) during the course of development. Expression of MHC was prominent by day 8, corresponding to the time when contracting cells became abundant in the culture.

Figure 4:
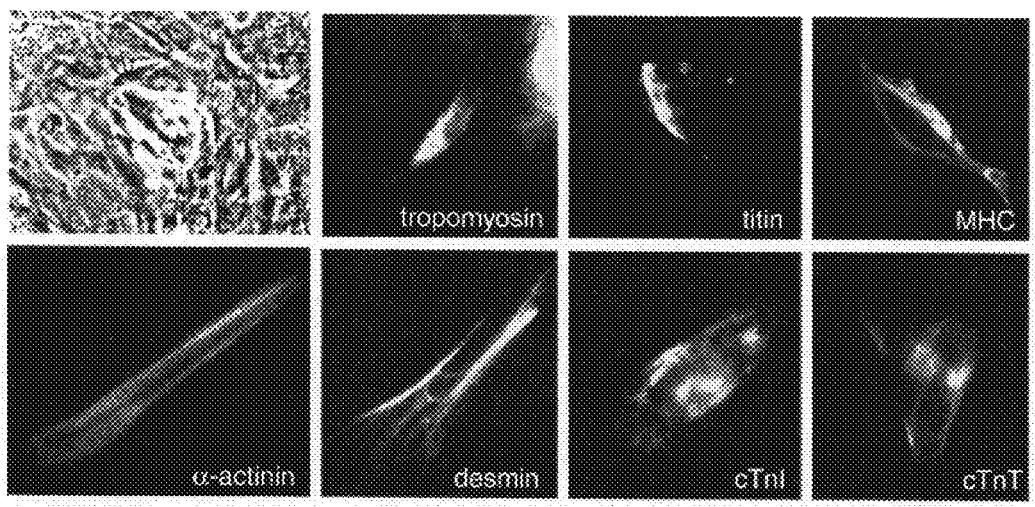

FIG. 4 shows single cells and cell clusters separated and stained for tropomyosin, titin, myosin heavy chain (MHC), α-actinin, desmin, cardiac troponin I (cTnI), and cardiac troponin T (cTnT). Single cells and clusters stained positive for all these markers. The striations characteristic of the sarcomeric structures can be seen, a feature that is consistent with the ability of the cells to exhibit contractile activity.

Figure 5:
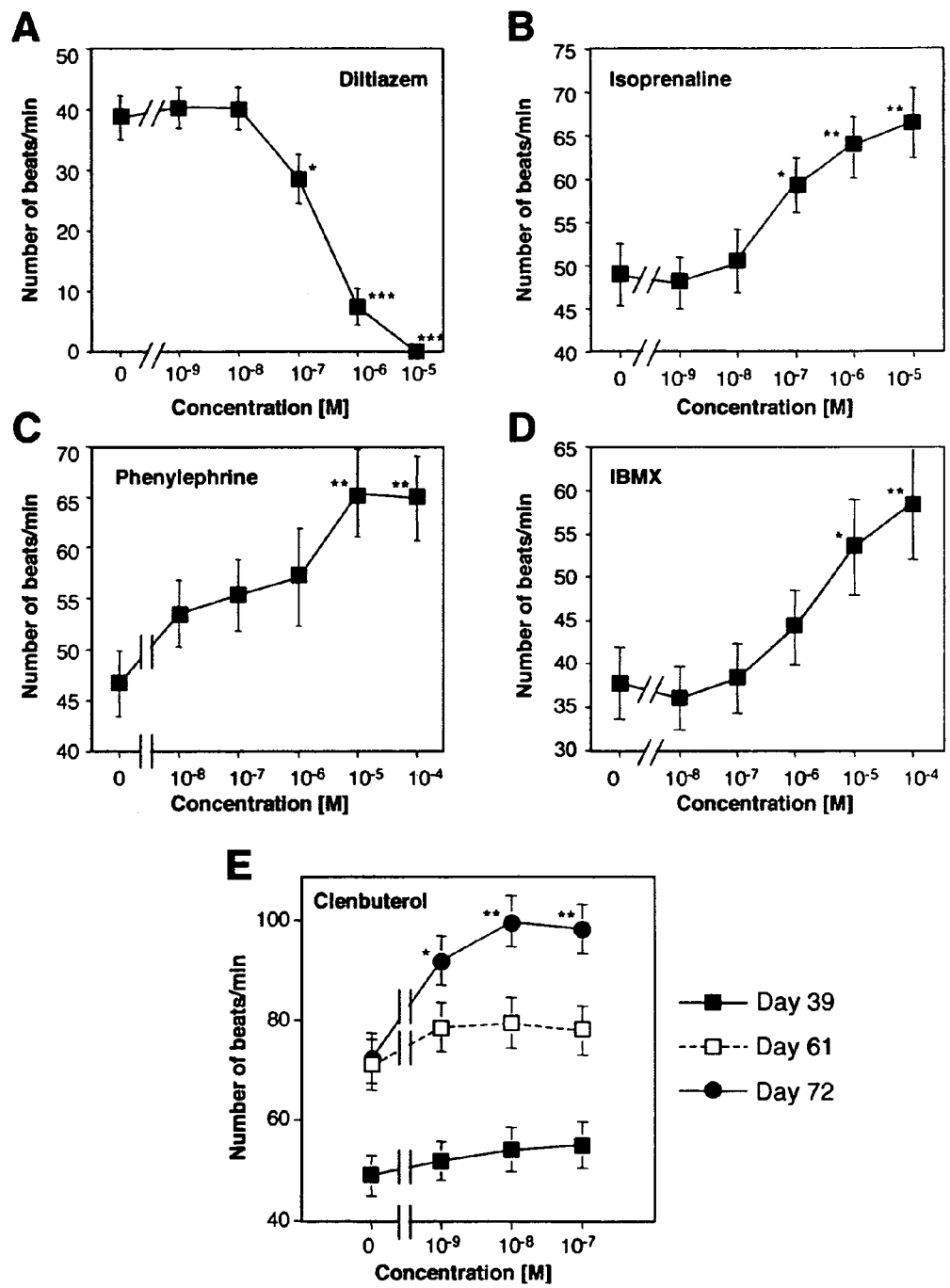

FIG. 5 shows the effect of pharmacological agents on contractile activity of the hES derived cardiomyocytes. The L-type calcium channel inhibitor diltiazem inhibited contractile activity in a dose-dependent fashion. The adrenoceptor agonists isoprenaline, phenylephrine, and clenbuterol had a chronotropic effect.

Figure 6:
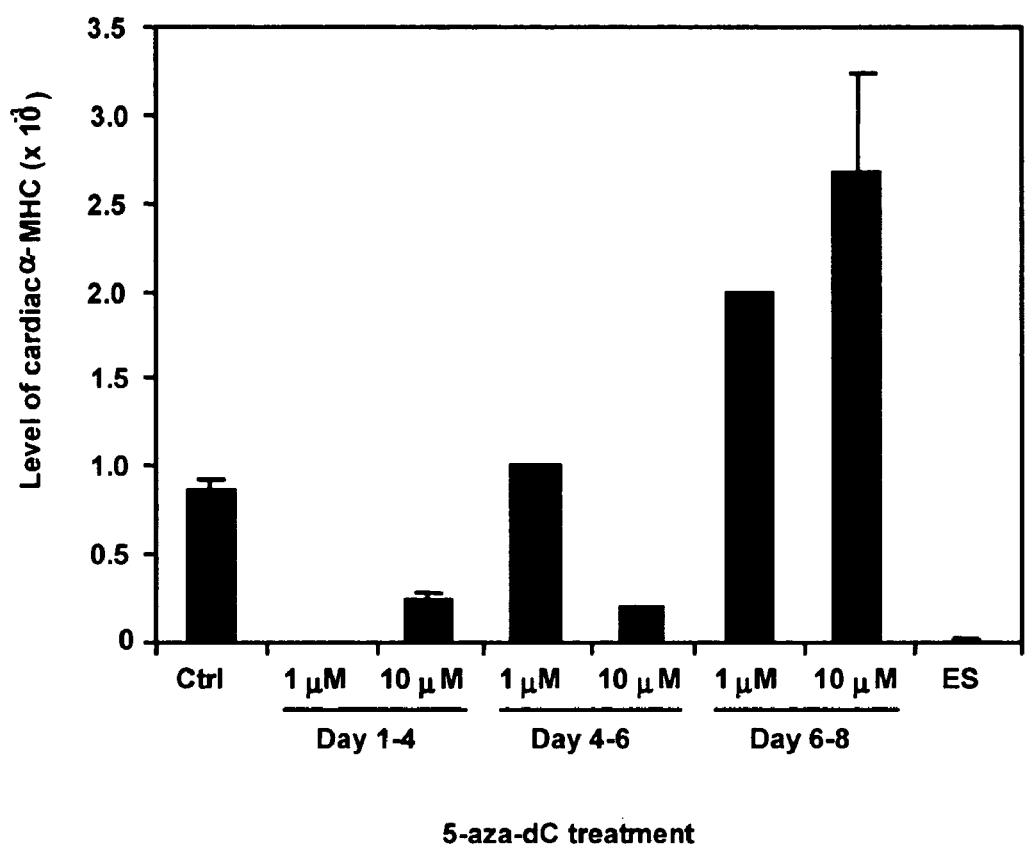

FIG. 6 shows the ability of the cytosine analog 5-aza-deoxy-cytidine to act as a cardiomyocyte differentiation induction agent. Embryoid bodies were formed from hES cells in suspension culture for 4 days, followed by plating on gelatin-coated plates. 5-aza-deoxy-cytidine was included in the culture medium during days 1-4, 4-6, or 6-8. The agent was most effective after differentiation of the hES cells was well underway.

Figure 7:
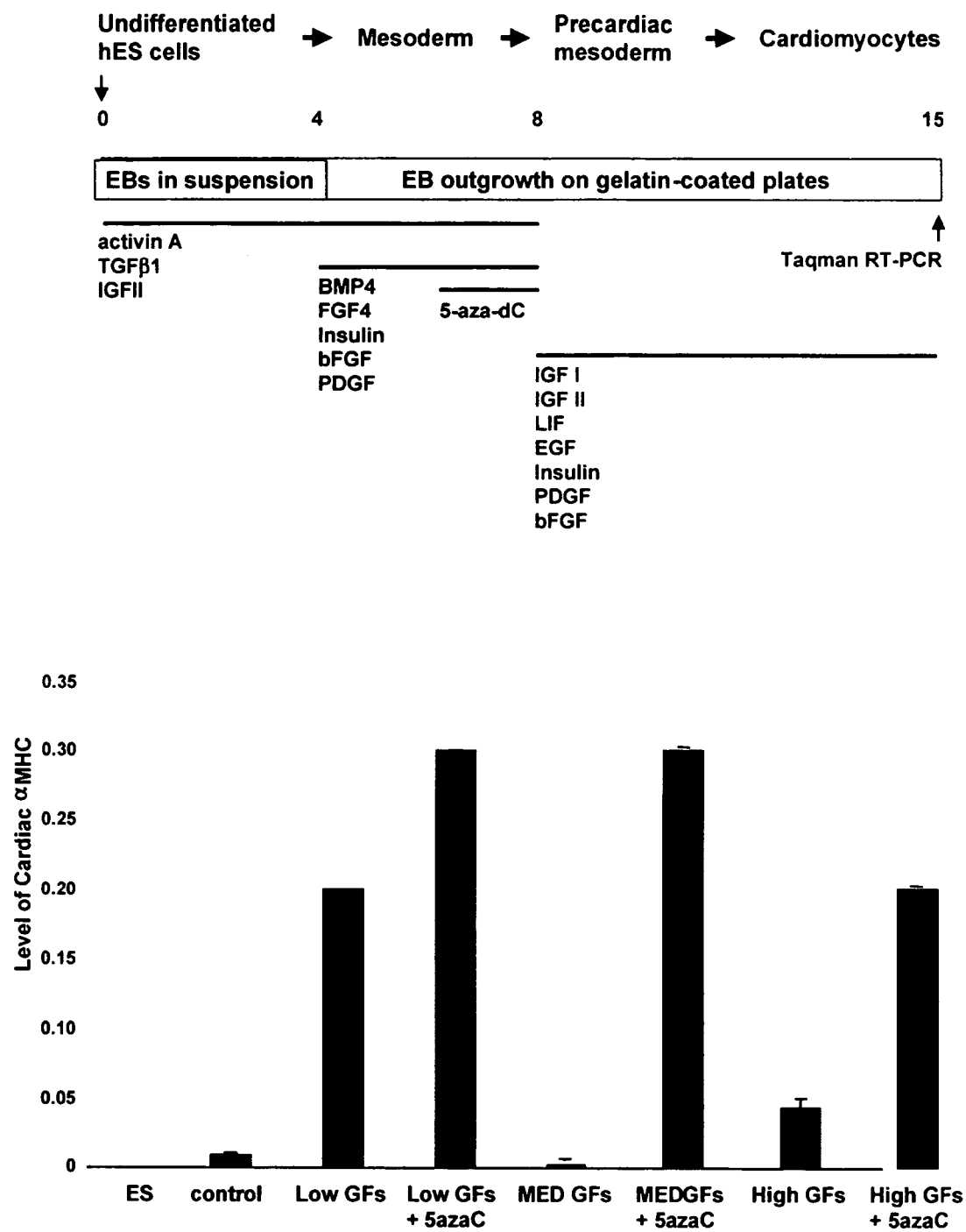

FIG. 7 illustrates the evaluation of potential cardiotropic factors for their ability to enhance the proportion of cardiomyocyte lineage cells in the population. Activins and certain growth factors were introduced during embryoid body formation (Group I); other growth factors (Group II) and 5-aza-deoxy-cytidine were introduced after plating onto gelatin; and additional factors (Group III) were added later during differentiation. The combinations were tested at three concentration levels. Most effective were low concentrations of growth factors in combination with 5-aza-deoxy-cytidine.

Figure 8A:
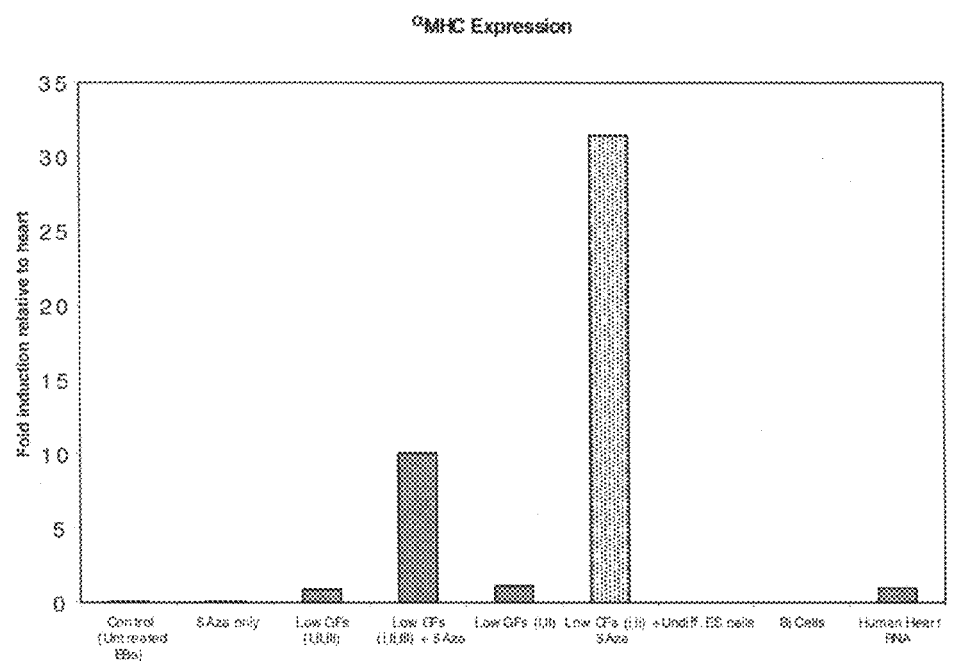
Figure 8A:
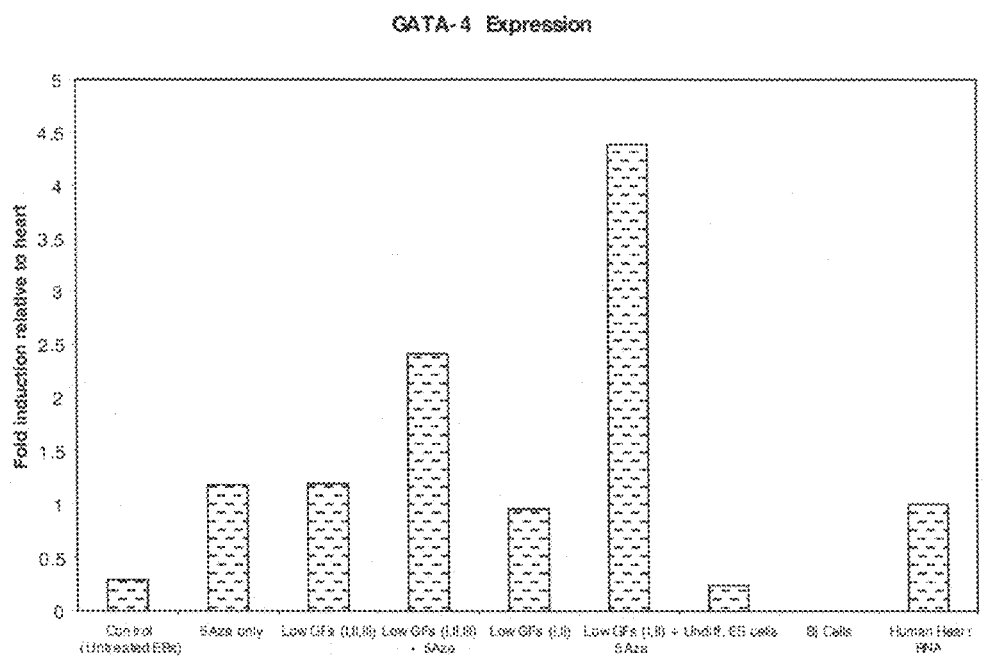
Figure 8B:
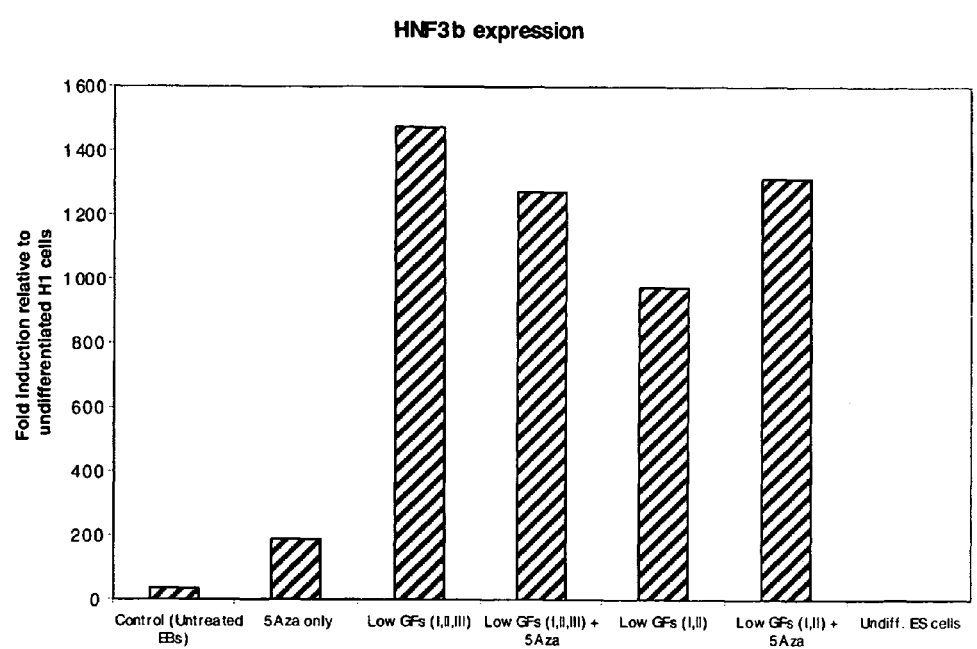

FIGS. 8(A) and 8(B) show further refinement of the protocol by adjusting each group of factors independently. The α-MHC marker characteristic of cardiomyocytes was most abundantly produced when the factors in Groups I and II were used at low levels and followed by 5-aza-deoxy-cytidine. Group III factors used later during differentiation actually inhibited cardiomyocyte formation. Expression of the early cardiomyocyte-associated gene GATA-4 was also improved under these conditions. The effect on α-MHC and GATA-4 was selective, in comparison with the endoderm-associated gene HNF3b, which increased using any growth factor combination, but not with 5-aza-deoxy-cytidine.

Figure 9:
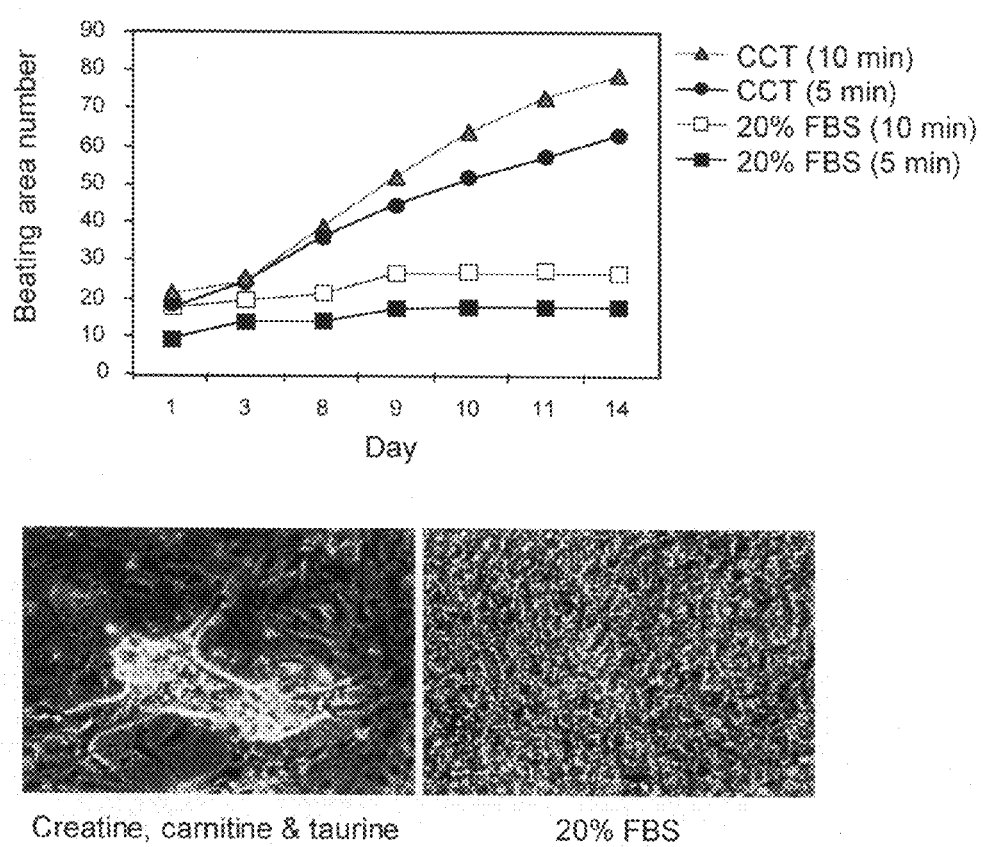

FIG. 9 shows the enrichment achieved by culturing populations containing cardiomyocytes for 1-2 weeks in a medium containing creatine, carnitine, and taurine (CCT). Each line represents the beating areas seen in a single well followed over the course of the experiment. The CCT medium enriches the number of beating areas in the culture by about 4-fold, compared with cells cultured in a standard differentiation medium.

Figure 10:
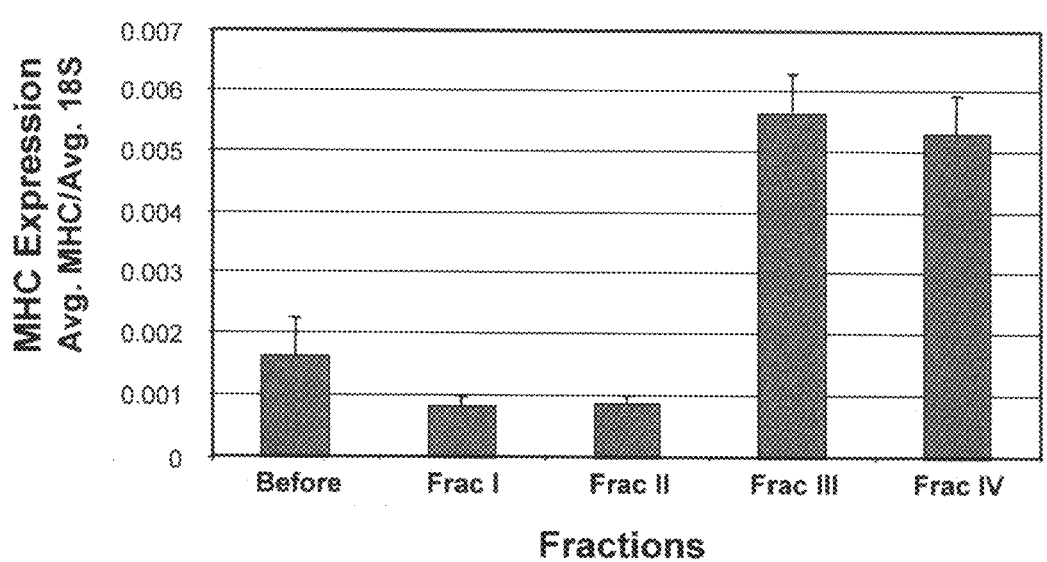

FIG. 10 shows the effect of separating a population of cells differentiated from hES cells on a discontinuous Percoll™ gradient. Fraction I. upper interface; II. 40.5% layer; III. lower interface; IV. 58.5% layer. As measured by real-time RT-PCR analysis, expression of the cardiomyocyte marker α-myosin heavy chain was highest in the higher density fractions.

Figure 11:
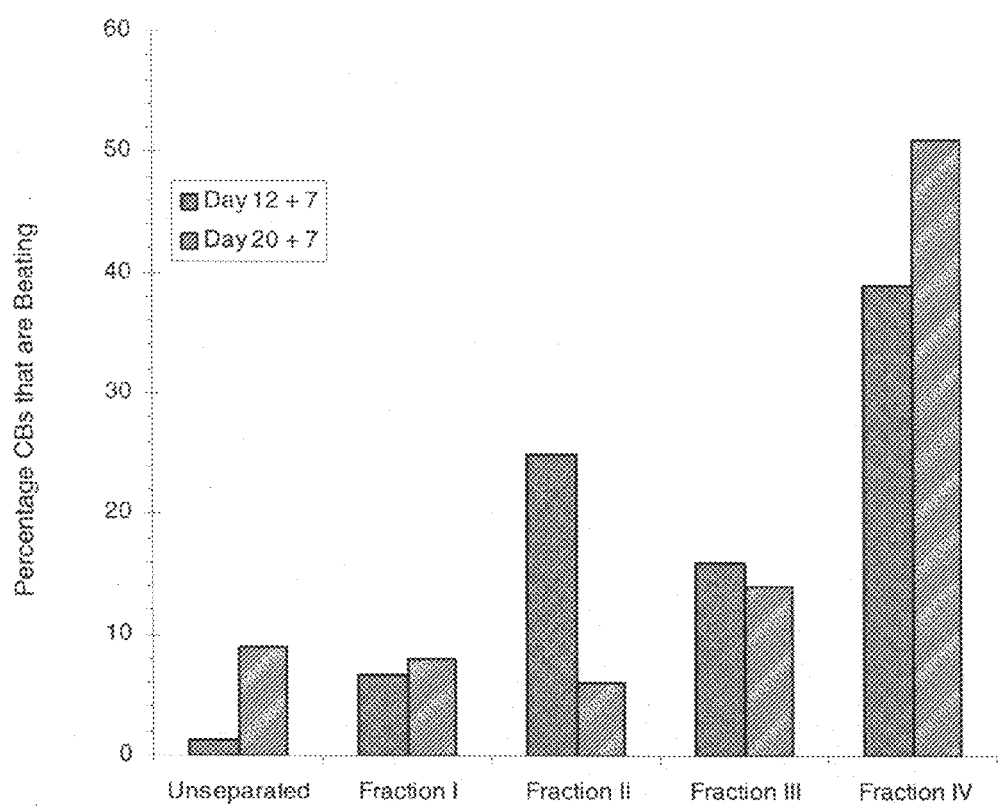

FIG. 11 shows the expression of cardiomyocyte markers MHC and cTnI in the Percoll™ fractions, relative to the unfractionated cells. Only Fraction IV shows substantial enrichment. Cardiac Bodies™ were then formed from the Fraction IV cells by separating clustered cells in the suspension, and culturing the clusters for an additional 8 days, periodically removing more single cells. This leads to a preparation of cells in which the level of MHC and cTnI expression has increased by 100- to 500-fold.

Figure 12:
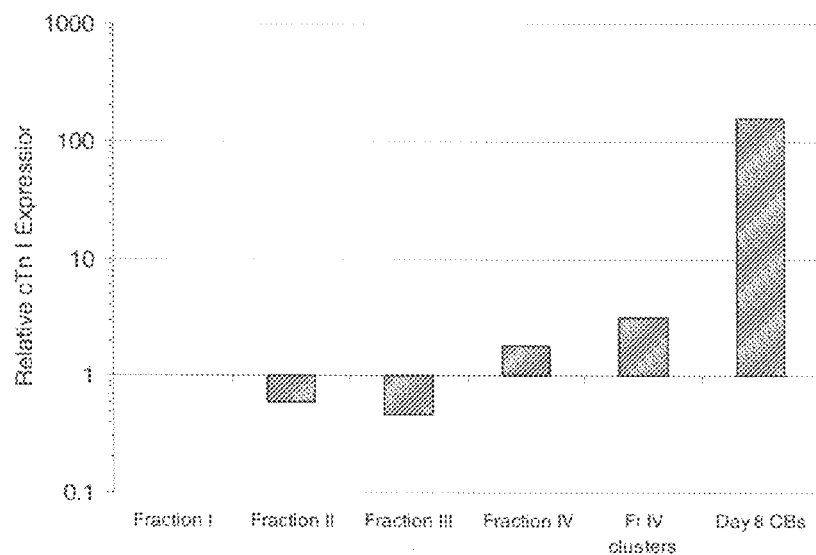
Figure 12:
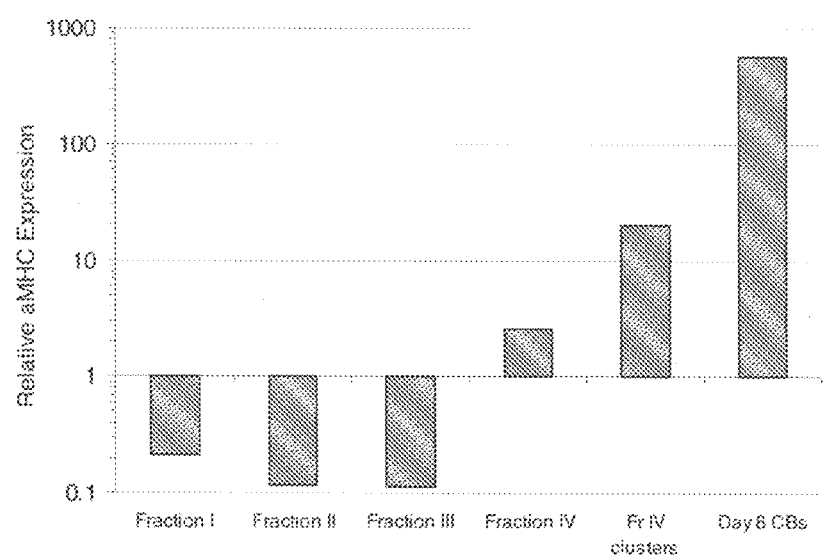

FIG. 12 shows the expression of cTnI measured in cardiac bodies formed from each of the four Percoll™ fractions. Undifferentiated hES cells are used as a negative control. Culturing as cardiac bodies enriched for cTnI expression in cardiac bodies made with Fraction IV cells.

Figure 13:
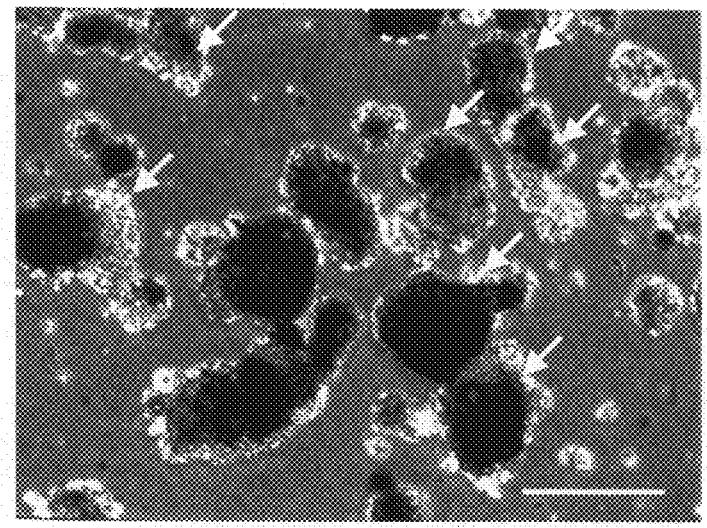

FIG. 13 shows a field of cardiac bodies made from Fraction IV cells (bar=300 μm). The clusters marked by the arrows were undergoing spontaneous contractions.

Figure 14:
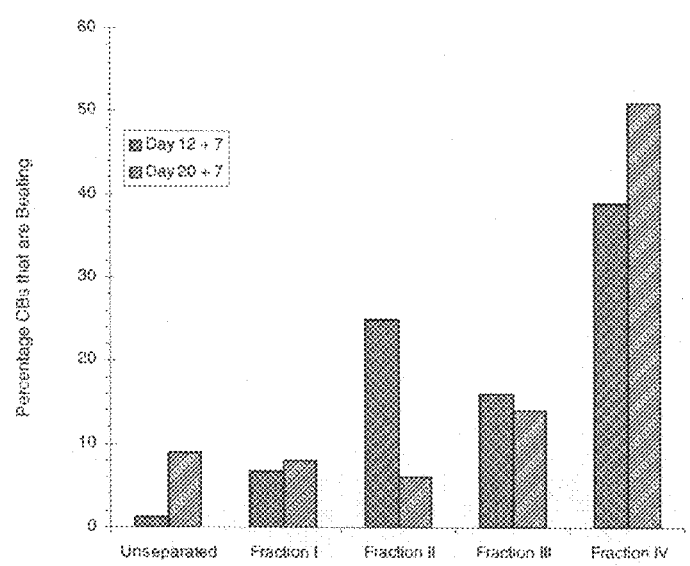

FIG. 14 shows the proportion of clusters that were beating when cardiac bodies were made from each of the Percoll™ fractions, following 12 or 20 days of differentiation. The combination of a 20 day differentiation period, separation of the highest density fraction, and subsequent culturing of the cardiac bodies for 7 days produced the highest proportion of clusters undergoing spontaneous contraction.

DETAILED DESCRIPTION

This invention provides a system for preparing and characterizing cardiomyocytes and their precursors from primate pluripotent stem cells.

A number of obstacles have stood in the way of developing a paradigm for obtaining substantially enriched populations of cardiomyocyte lineage cells from primate pluripotent stem (pPS) cells. Some ensue from the relative fragility of pluripotent cells of primate origin, the difficulty in culturing them, and their exquisite sensitivity and dependence on various factors present in the culture environment. Other obstacles ensue from the understanding that cardiac progenitor cells require visceral embryonic endoderm and primitive streak for terminal differentiation (Arai et al., Dev. Dynamics 210:344, 1997). In order to differentiate pPS cells into cardiac progenitor cells in vitro, it will be necessary to mimic or substitute for all the events that occur in the natural ontogeny of such cells in the developing fetus.

In spite of these obstacles, it has now been discovered that populations of cells can be obtained from pPS cultures that are considerably enriched for cells expressing characteristics of cardiac cells. FIG. 4 shows individual cells stained for tropomyosin, titin, myosin heavy chain (MHC), α-actinin, desmin, cardiac troponin I (cTnI), and cardiac troponin T (cTnT), and showing striations characteristic of sarcomeric structures. The cells undergo spontaneous periodic contraction in tissue culture. FIG. 5 shows that the contractile activity is inhibited by the L-type calcium channel inhibitor diltiazem, and increases in response to adrenoceptor agonists isoprenaline and phenylephrine.

It is clear that the pathway for making cardiomyocytes from human pluripotent stem cells differs in a number of ways from pathways previously described for making mouse cardiomyocytes. First of all, the proliferation of human pPS cells in an undifferentiated state and ready for cardiomyocyte differentiation requires a different culture system. Mouse embryonic stem cells can be propagated without differentiation by simply including leukemia inhibitory factor (LIF) in the medium. Yet LIF is insufficient by itself to prevent the differentiation of human ES cells, which conventionally are propagated on a feeder layer of primary embryonic fibroblasts (Thomson et al., supra). Furthermore, factors that generate cardiomyocytes from mouse stem cells, such as retinoic acid (Wobus et al., J. Mol. Cell Cardiol. 29:1525, 1997) and DMSO (McBurney et al., Nature 299:165, 1982), are much less effective when used with human stem cells under similar conditions (Example 6).

This invention solves the problem of making important derivative cells from human pluripotent stem cells by providing a new system that permits highly enriched populations of cardiomyocyte lineage cells to be obtained. The system readily lends itself to implementation on a commercial scale. Procedures that can be used to enhance cardiomyocyte production include:

1. Putting undifferentiated pPS cells through a culture paradigm (either forming embryoid bodies or by direct differentiation) that initiates the differentiation process.
2. Culturing the cells in the presence of one or more cardiotropic factors, which are believed to help drive the cells into the cardiomyocyte lineage.
3. Separating cardiomyocytes from other cells by density centrifugation or another suitable separation means.
4. Reculturing the separated cells so as to further expand or enrich the proportion of cardiomyocyte cells—for example, by removing single cells from the culture and culturing the cells that cluster together as Cardiac Bodies™.

Steps such as these and others described in this disclosure can be used alone or in any effective combination. As illustrated in Example 9, just a few of these strategies in combination provide novel cell populations comprising over 69% cardiomyocyte lineage cells.

The remarkable uniformity and functional properties of the cells produced according to this disclosure make them valuable for developing new therapeutic modalities and as a tool for studying cardiac tissue in vitro.

DEFINITIONS

The techniques and compositions of this invention relate to pPS-derived cardiomyocytes and their precursors. Phenotypic characteristics of cardiomyocytes are provided in a later section of this disclosure. There are no particular characteristics that are definitive for cardiomyocyte precursors, but it is recognized that in the normal course of ontogeny, undifferentiated pPS cells first differentiate into mesodermal cells, and then through various precursor stages to a functional (end-stage) cardiomyocyte.

Accordingly, for the purposes of this disclosure, a "cardiomyocyte precursor" is defined as a cell that is capable (without dedifferentiation or reprogramming) of giving rise to progeny that include cardiomyocytes, and which expresses at least one marker (and preferably at least 3 or 5 markers) from the following list: cardiac troponin I (cTnI), cardiac troponin T (cTnT), sarcomeric myosin heavy chain (MHC), GATA-4, Nkx2.5, N-cadherin, β1-adrenoceptor (β1-AR), ANF, the MEF-2 family of transcription factors, creatine kinase MB (CK-MB), myoglobin, or atrial natriuretic factor (AN F).

Throughout this disclosure, techniques and compositions that refer to "cardiomyocytes" or "cardiomyocyte precursors" can be taken to apply equally to cells at any stage of cardiomyocyte ontogeny without restriction, as defined above, unless otherwise specified. The cells may or may not have the ability to proliferate or exhibit contractile activity.

Certain cells of this invention demonstrate spontaneous periodic contractile activity. This means that when they are cultured in a suitable tissue culture environment with an appropriate $Ca^{++}$ concentration and electrolyte balance, the cells can be observed to contract in a periodic fashion across one axis of the cell, and then release from contraction, without having to add any additional components to the culture medium.

The term Cardiac Body™ (used in the singular or plural) has been created by Geron Corporation as a term or brand for a cardiomyocyte cluster—more specifically, a cluster of pPS derived cells in suspension, bearing two or more characteristics of human cardiomyocyte lineage cells. A substantial proportion of cells in the cluster express cTnI, cTnT, ANF, or MHC from an endogenous gene, and the cluster usually undergoes spontaneous contraction in the presence of $Ca^{++}$ and appropriate electrolytes. The cardiomyocyte cluster may be present in a cell culture, in a pharmaceutical preparation, or any other useful composition. This disclosure allows the user to prepare suspensions of Cardiac Bodies™ in which well over 50% undergo spontaneous contraction Prototype "primate Pluripotent Stem cells" (pPS cells) are pluripotent cells derived from any kind of embryonic tissue (fetal or pre-fetal tissue), and have the characteristic of being capable under appropriate conditions of producing progeny of different cell types that are derivatives of all of the 3 germinal layers (endoderm, mesoderm, and ectoderm), according to a standard art-accepted test, such as the ability to form a teratoma in 8-12 week old SCID mice, or the ability to form identifiable cells of all three germ layers in tissue culture.

Included in the definition of pPS cells are embryonic cells of various types, exemplified by human embryonic stem (hES) cells, described by Thomson et al. (Science 282:1145, 1998); embryonic stem cells from other primates, such as Rhesus stem cells (Thomson et al., Proc. Natl. Acad. Sci. USA 92:7844, 1995), marmoset stem cells (Thomson et al., Biol. Reprod. 55:254, 1996) and human embryonic germ (hEG) cells (Shamblott et al., Proc. Natl. Acad. Sci. USA 95:13726, 1998). These cell types may be provided in the form of an established cell line, or they may be obtained directly from primary embryonic tissue and used immediately for differentiation. Other types of pluripotent cells are also included in the term. Any cells of primate origin that are capable of producing progeny that are derivatives of all three germinal layers are included, regardless of whether they were derived from embryonic tissue, fetal tissue, or other sources. The pPS cells are not derived from a malignant source. It is desirable (but not always necessary) that the cells be karyotypically normal.

pPS cell cultures are described as "undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view in colonies of cells with high nuclear/cytoplasmic ratios and prominent nucleoli. It is understood that colonies of undifferentiated cells within the population will often be surrounded by neighboring cells that are differentiated.

In the context of cell ontogeny, the adjective "differentiated" is a relative term. A "differentiated cell" is a cell that has progressed further down the developmental pathway than the cell it is being compared with. Thus, pluripotent embryonic stem cells can differentiate to lineage-restricted precursor cells (such as a mesodermal stem cell), which in turn can differentiate into other types of precursor cells further down the pathway (such as an cardiomyocyte precursor), and then to an end-stage differentiated cell, which plays a characteristic role in a certain tissue type, and may or may not retain the capacity to proliferate further.

"Feeder cells" or "feeders" are terms used to describe cells of one type that are co-cultured with cells of another type, to provide an environment in which the cells of the second type can grow. pPS cell populations are said to be "essentially free" of feeder cells if the cells have been grown through at least one round after splitting in which fresh feeder cells are not added to support the growth of the pPS. It is recognized that if a previous culture containing feeder cells is used as a source of pPS for a new culture containing no feeder cells, there will be some feeder cells that survive the passage. The culture is essentially free of feeder cells when there is less than ~5% surviving feeder cells present. Compositions containing less than 1%, 0.2%, 0.05%, or 0.01% feeder cells (expressed as % of total cells in the culture) are increasingly more preferred. When a cell line spontaneously differentiates in the same culture into multiple cell types, the different cell types are not considered to act as feeder cells for each other within the meaning of this definition, even though they may interact in a supportive fashion.

A "growth environment" is an environment in which cells of interest will proliferate, differentiate, or mature in vitro. Features of the environment include the medium in which the cells are cultured, any growth factors or differentiation-inducing factors that may be present, and a supporting structure (such as a substrate on a solid surface) if present.

A cell is said to be "genetically altered" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

The term "antibody" as used in this disclosure refers to both polyclonal and monoclonal antibody. The ambit of the term deliberately encompasses not only intact immunoglobulin molecules, but also such fragments and derivatives of immunoglobulin molecules (such as single chain Fv constructs, diabodies, and fusion constructs) as may be prepared by techniques known in the art, and retaining a desired antibody binding specificity.

General Techniques

For further elaboration of general techniques useful in the practice of this invention, the practitioner can refer to standard textbooks and reviews in cell biology, tissue culture, embryology, and cardiophysiology.

With respect to tissue culture and embryonic stem cells, the reader may wish to refer to *Teratocarcinomas and embryonic stem cells: A practical approach* (E. J. Robertson, ed., IRL Press Ltd. 1987); *Guide to Techniques in Mouse Development* (P. M. Wasserman et al. eds., Academic Press 1993); *Embryonic Stem Cell Differentiation in Vitro* (M. V. Wiles, Meth. Enzymol. 225:900, 1993); *Properties and uses of Embryonic Stem Cells: Prospects for Application to Human Biology and Gene Therapy* (P. D. Rathjen et al., Reprod. Fertil. Dev. 10:31, 1998). With respect to the culture of heart cells, standard references include *The Heart Cell in Culture* (A. Pinson ed., CRC Press 1987), *Isolated Adult Cardiomyocytes* (Vols. I & II, Piper & Isenberg eds., CRC Press 1989), *Heart Development* (Harvey & Rosenthal, Academic Press 1998), *I Left my Heart in San Francisco* (T. Bennet, Sony Records 1990); and *Gone with the Wnt* (M. Mitchell, Scribner 1996).

General methods in molecular and cellular biochemistry can be found in such standard textbooks as *Molecular Cloning: A Laboratory Manual,* 3rd Ed. (Sambrook et al., Harbor Laboratory Press 2001); *Short Protocols in Molecular Biology,* 4th Ed. (Ausubel et al. eds., John Wiley & Sons 1999); *Protein Methods* (Bollag et al., John Wiley & Sons 1996); *Nonviral Vectors for Gene Therapy* (Wagner et al. eds., Academic Press 1999); *Viral Vectors* (Kaplift & Loewy eds., Academic Press 1995); *Immunology Methods Manual* (I. Lefkovits ed., Academic Press 1997); and *Cell and Tissue Culture: Laboratory Procedures in Biotechnology* (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Sources of Stem Cells

This invention can be practiced with pluripotent stem cells of various types, particularly stem cells derived from embryonic tissue and have the characteristic of being capable of producing progeny of all of the three germinal layers, as described above.

Exemplary are embryonic stem cells and embryonic germ cells used as existing cell lines or established from primary embryonic tissue of a primate species, including humans. This invention can also be practiced using pluripotent cells obtained from primary embryonic tissue, without first establishing an undifferentiated cell line.

Embryonic Stem Cells

Embryonic stem cells can be isolated from blastocysts of primate species (U.S. Pat. No. 5,843,780; Thomson et al., Proc. Natl. Acad. Sci. USA 92:7844, 1995). Human embryonic stem (hES) cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. Equivalent cell types to hES cells include their pluripotent derivatives, such as primitive ectoderm-like (EPL) cells, outlined in WO 01/51610 (Bresagen).

hES cells can be obtained from human preimplantation embryos (Thomson et al., Science 282:1145, 1998). Alternatively, in vitro fertilized (IVF) embryos can be used, or one-cell human embryos can be expanded to the blastocyst stage (Bongso et al., Hum Reprod 4: 706, 1989). Embryos are cultured to the blastocyst stage, the zona pellucida is removed, and the inner cell masses are isolated (for example, by immunosurgery using rabbit anti-human spleen cell antiserum). The intact inner cell mass is plated on mEF feeder layers, and after 9 to 15 days, inner cell mass derived outgrowths are dissociated into clumps. Growing colonies having undifferentiated morphology are dissociated into clumps, and replated. ES-like morphology is characterized as compact colonies with apparently high nucleus to cytoplasm ratio and prominent nucleoli. Resulting ES cells are then routinely split every 1-2 weeks. Clump sizes of about 50 to 100 cells are optimal.

Propagation of pPS Cells in an Undifferentiated State pPS cells can be propagated continuously in culture, using culture conditions that promote proliferation while inhibiting differentiation. Exemplary serum-containing ES medium is made with 80% DMEM (such as Knock-Out DMEM, Gibco), 20% of either defined fetal bovine serum (FBS, Hyclone) or serum replacement (US 2002/0076747 A1, Life Technologies Inc.), 1% non-essential amino acids, 1 mM L-glutamine, and 0.1 mM β-mercaptoethanol.

Traditionally, ES cells are cultured on a layer of feeder cells, typically fibroblasts derived from embryonic or fetal tissue (Thomson et al., Science 282:1145, 1998). Scientists at Geron have discovered that pPS cells can be maintained in an undifferentiated state even without feeder cells. The environment for feeder-free cultures includes a suitable culture substrate, particularly an extracellular matrix such as Matrigel® or laminin. The pPS cells are plated at >15,000 cells $cm^{-2}$ (optimally 90,000 $cm^{-2}$ to 170,000 $cm^{-2}$). Typically, enzymatic digestion is halted before cells become completely dispersed (say, ~5 min with collagenase IV). Clumps of ~10 to 2,000 cells are then plated directly onto the substrate without further dispersal. Alternatively, the cells can be harvested without enzymes before the plate reaches confluence by incubating ~5 min in a solution of 0.5 mM EDTA in PBS. After washing from the culture vessel, the cells are plated into a new culture without further dispersal. In a further illustration, confluent hES cells cultured in the absence of feeders are removed from the plates by incubating with a solution of 0.05% (wt/vol) trypsin (Gibco) and 0.053 mM EDTA for 5-15 min at 37° C. The remaining cells in the plate are removed and the cells are triturated into a suspension comprising single cells and small clusters, and then plated at densities of 50,000-200,000 cells $cm^{-2}$ to promote survival and limit differentiation.

Feeder-free cultures are supported by a nutrient medium containing factors that promote proliferation of the cells without differentiation (WO 99/20741). Such factors may be introduced into the medium by culturing the medium with cells secreting such factors, such as irradiated (~4,000 rad) primary mouse embryonic fibroblasts, telomerized mouse fibroblasts, or fibroblast-like cells derived from pPS cells (U.S. Pat. No. 6,642,048). Medium can be conditioned by plating the feeders in a serum free medium such as KO DMEM supplemented with 20% serum replacement and 4 ng/mL bFGF. Medium that has been conditioned for 1-2 days is supplemented with further bFGF, and used to support pPS cell culture for 1-2 days (WO 01/51616; Xu et al., Nat. Biotechnol. 19:971, 2001).

Alternatively, fresh or non-conditioned medium can be used, which has been supplemented with added factors (like a fibroblast growth factor or forskolin) that promote proliferation of the cells in an undifferentiated form. Exemplary is a base medium like X-VIVO™ 10 (Biowhittaker) or QBSF™-60 (Quality Biological Inc.), supplemented with bFGF at 40-80 ng/mL, and optionally containing stem cell factor (15 ng/mL), or Flt3 ligand (75 ng/mL). These medium formulations have the advantage of supporting cell growth at 2-3 times the rate in other systems.

Under the microscope, ES cells appear with high nuclear/cytoplasmic ratios, prominent nucleoli, and compact colony formation with poorly discernable cell junctions. Primate ES cells typically express the stage-specific embryonic antigens (SSEA) 3 and 4, and markers detectable using antibodies designated Tra-1-60 and Tra-1-81. Undifferentiated hES cells also typically express the transcription factor Oct-3/4, Cripto, gastrin-releasing peptide (GRP) receptor, podocalyxin-like protein (PODXL), and human telomerase reverse transcriptase (hTERT) (US 2003/0224411 A1), as detected by RT-PCR.

Procedures for Preparing Cardiomyocytes

Cells of this invention can be obtained by culturing or differentiating stem cells in a special growth environment that enriches for cells with the desired phenotype (either by outgrowth of the desired cells, or by inhibition or killing of other cell types). These methods are applicable to many types of stem cells, especially primate pluripotent stem (pPS) cells described in the previous section.

Differentiation is typically initiated by formation of embryoid bodies or aggregates: for example, by overgrowth of a donor pPS cell culture, or by culturing pPS cells in suspension in culture vessels having a substrate with low adhesion properties which allows EB formation. pPS cells are harvested by brief collagenase digestion, dissociated into clusters, and plated in non-adherent cell culture plates. The aggregates are fed every few days, and then harvested after a suitable period, typically 4-8 days. The harvested aggregates are then plated onto a solid substrate, and cultured for a period that allows cells within the aggregates to adopt a cardiomyocyte phenotype. Typically, the total differentiation period is at least 8 days, and may be at least 10 or 12 days in length. Optionally, the EBs can be produced encapsulated in alginate or other suitable nutrient-permeable matrix, which may help improve the uniformity of EB diameter and consistency of the cells produced (WO 03/004626, Zandstra et al.).

The differentiation process can also be initiated by culturing the cells in a differentiation paradigm. In the direct differentiation method, the culture environment is changed to induce differentiation, or remove the elements that keep the pPS in the undifferentiated state (WO 01/51616). For making cardiomyocytes, adding ~20% fetal bovine serum to the medium generates foci of contracting cells of the cardiomyocyte lineage. Other non-specific differentiation inducing agents such as retinoic acid (RA) or dimethyl sulfoxide (DMSO) can also be added. Caution is advised, however, since some alternatives may reduce the proportion of cardiomyocytes obtained (Example 6).

It is also sometimes beneficial to include in the medium one or more "cardiotropic factors". These are factors that either alone or in combination enhance proliferation or survival of cardiomyocyte type cells, or inhibit the growth of other cell types. The effect may be due to a direct effect on the cell itself, or due to an effect on another cell type, which in turn enhances cardiomyocyte formation. For example, factors that induce the formation of hypoblast or epiblast equivalent cells, or cause these cells to produce their own cardiac promoting elements, all come within the rubric of cardiotropic factors.

Factors thought to induce differentiation of pPS cells into cells of the mesoderm layer, or facilitate further differentiation into cardiomyocyte lineage cells include the following:

- Nucleotide analogs that affect DNA methylation and altering expression of cardiomyocyte-related genes
- TGF-β ligands (exemplified by TGF-β1, TGF-β2, TGF-β3 and other members of the TGF-β superfamily illustrated below). Ligands bind a TGF-β receptor activate Type I and Type II serine kinases and cause phosphorylation of the Smad effector.
- Morphogens like Activin A and Activin B (members of the TGF-β superfamily)
- Insulin-like growth factors (such as IGF II)
- Bone morphogenic proteins (members of the TGF-β superfamily, exemplified by BMP-2 and BMP-4)
- Fibroblast growth factors (exemplified by bFGF, FGF-4, and FGF-8) and other ligands that activate cytosolic kinase raf-1 and mitogen-activated proteins kinase (MAPK)
- oxytocin (and other ligands that activate the same hormonal response)
- Platelet-derived growth factor (exemplified by PDGFβ)
- Natriuretic factors (exemplified by atrial natriuretic factor (ANF), brain natriuretic peptide (BNP).
- Related factors such as insulin, leukemia inhibitory factor (LIF), epidermal growth factor (EGF), TGFα, and products of the cripto gene
- Specific antibodies with agonist activity for the same receptors Alternatively or in addition, the cells can be cocultured with cells (such as endothelial cells of various kinds) that secrete factors enhancing cardiomyocyte differentiation.

As illustrated in Example 6, nucleotide analogs that affect DNA methylation (and thereby influence gene expression) can effectively be used to increase the proportion of cardiomyocyte lineage cells that emerge following initial differentiation. For example, it has been found that inclusion of 5-aza-deoxy-cytidine in the culture medium increases the frequency of contracting cells in the population, and expression of cardiac MHC—either from embryoid body cells, or in the direct differentiation protocol.

The evaluation of cardiotropic agents is further illustrated in Example 7. Particularly effective combinations of cardiotropic agents include use of a morphogen like Activin A and a plurality of growth factors, such as those included in the TGF-β and IGF families during the early commitment stage, optionally supplemented with additional cardiotropins such as one or more fibroblast growth factors, bone morphogenic proteins, and platelet-derived growth factors.

During the elaboration of this invention, it was found that omitting factors such as insulin-like growth factor II (IGF II) and related molecules from the final stages of in vitro differentiation actually increased the levels of cardiac gene expression. In unrelated studies, IGF II has been found to decrease the levels of GSK3β in fibroblasts (Scalia et al., J. Cell. Biochem. 82:610, 2001). IGF II may therefore potentiate the effects of Wnt proteins present in the culture medium or secreted by the cells. Wnt proteins normally stabilize and cause nuclear translocation of a cytoplasmic molecule, β catenin, which comprises a portion of the transcription factor TCF. This changes transcriptional activity of multiple genes. In the absence of Wnt, β catenin is phosphorylated by the kinase GSK3β, which both destabilizes β catenin and keeps it in the cytoplasm.

Since Wnt activators like IL II apparently limit cardiomyocyte differentiation, it is believed that culturing with Wnt antagonists can increase the extent or proportion of cardiomyocyte differentiation of hES cells. Wnt signaling can be inhibited by injection of synthetic mRNA encoding either DKK-1 or Crescent (secreted proteins that bind and inactivate Wnts) (Schneider et al., Genes Dev. 15:304, 2001), or by infection with a retrovirus encoding DKK-1 (Marvin et al., Genes Dev. 15:316, 2001). Alternatively, the Wnt pathway can be inhibited by increasing the activity of the kinase GSK3β, for example, by culturing the cells with factors such as IL-6 or glucocorticoids.

Of course, it is not usually necessary to understand the mode of action of a cardiotropic factor in order to employ it in a differentiation paradigm according to this invention. The combinations and amounts of such compounds that are effective for enriching cardiomyocyte production can be determined empirically by culturing undifferentiated or early differentiated hES cells or their progeny in a culture environment incorporating such factors, and then determining whether the compound has increased the number of cardiomyocyte lineage cells in the population according to the phenotypic markers listed below.

Example 2 and Example 5 show that differentiation of pPS into cardiomyocyte lineage cells occurs efficiently in the presence of fetal bovine serum. In certain circumstances, the use of serum or a serum substitute or replacement at an appropriate concentration in the medium (usually 5 to 40%, typically 20%) is sufficient to promote the differentiation process, with the use of other added cardiotrophic factors being optional. Candidate serum substitutes include those described in Desai et al., Hum. Reprod. 12:328, 1997; Gardner, Hum. Reprod. 13 Suppl. 4:218, 1998; and US 20020076747 A1. It has also been discovered that inhibition of Wnt pathways by overexpression of the inhibitor Dkk-1 blocks cardiac differentiation. Cardiomyocytes appear in EB cultures under serum-free conditions if a Bone Morphogenic Protein (BMP) is added to the medium. Accordingly, medium containing nutrients and a BMP can substitute for serum, or can complement its effect in promoting cardiomyocyte generation and maturation.

pPS-derived cardiomyocytes can be separated into single-cell suspensions for purposes of replating and expansion, enrichment, cloning, and determination of phenotypic characteristics. Example 2 illustrates the preparation of single isolated cardiomyocytes using collagenase B solution. Also suitable are Collagenase II, or a mixture of collagenases such as Blendzyme IV (Roche). After the dissociation, cells were seeded into chamber slides and cultured in differentiation medium. The recultured single cardiomyocyte cells survived and continued to beat.

Suspensions of pPS-derived cells can be further enriched for cells with desirable characteristics, such as mechanical separation or cell sorting. It has been discovered that the percentage of contracting cells can be enriched by ~20-fold by density separation. Isolation of enriched cardiomyocyte populations by isopycnic centrifugation is illustrated in Examples 4 and 9. Starting with cells that have been differentiated for 8 to 30 days or longer, populations can be obtained that comprise at least ~5%, ~20%, ~60%, and potentially over ~90% cells of the cardiomyocyte lineage. Many of the research and therapeutic applications referred to in this disclosure benefit from enrichment of the proportion of cardiomyocytes, but that complete homogeneity is often not required.

Following initial differentiation (and before or after a separation step, if employed), the user has the option of increasing the percentage of cardiomyocyte lineage cells by culturing in an environment containing a "cardiomyocyte enrichment agent". This is simply a factor in the medium or on a surface substrate that promotes the outgrowth of the desired cell type—either by facilitating proliferation of cardiomyocyte lineage cells, or by inhibiting the growth (or causing apoptosis) of cells of other tissue types. Some of the cardiotropic factors listed above are suitable for this purpose. Also suitable are certain compounds known beneficial to cardiomyocytes in vivo, or their analogs. Included are compounds capable of forming a high energy phosphate bond (such as creatine); an acyl group carrier molecule (such as carnitine); and a cardiomyocyte calcium channel modulator (such as taurine).

Formation of Cardiac Bodies™

It has been discovered that preparations of pPS derived cardiomyocytes can be further expanded or enriched by allowing them to grow in clusters that are referred to as Cardiac Bodies™.

Once the cell population begins to show phenotypic characteristics of cardiomyocyte lineage cells, they are allowed to form clusters, and single cells in the suspension are removed. This can be accomplished by letting the clusters settle, and pipetting out the supernatant containing single cells. The clusters are then refed with culture medium (exemplified by medium containing fetal bovine serum, serum substitute, or CCT as described earlier). Culturing then continues with the cells remaining as clusters of 10 to 5000 cells (typically 50 to 1000 cells) in size.

After a suitable period (typically 1 to 7 days), the cultured cells can be harvested for characterization, or used in drug screening or pharmaceutical manufacture. The effect generally improves if the cells are taken through further cycles of removing single cells and reculturing the clusters, over a period of 8 days or more. Each cycle can optionally incorporate a step in which the clusters of cells are dispersed into single cells, or smaller cell clusters, to allow for further expansion. Larger clusters may form, either by aggregation of the suspended cells, or by proliferation within the cluster, or both. It is a hypothesis of this invention that cardiomyocyte lineage cells have a tendency to form such clusters under appropriate conditions, and that the removal of single cells helps eliminate other cell types and increase homogeneity.

Examples 10 and 11 illustrate the process. Mixed populations of cells containing cardiomyoctyes were put in fresh medium, and the clusters were harvested by settling in a 15 or 50 mL conical tube. They were refed in serum-containing medium, and taken through cycles of cluster separation, feeding, and reculturing every 2 or 3 days. After about 8 days, there was considerably increased expression of cardiomyocotye markers cTnI and MHC at the mRNA level (FIG. 12), and a high proportion of spontaneously contracting clusters (FIGS. 13 and 14).

The Cardiac Body™ technique can be used to expand and/or enrich the cardiomyocytes in the cell population at any time in the differentiation process. As exemplified below, the technique is particulary effective employed after a previous enrichment step by density separation. Implementation of the technique has benefits that were not anticipated before the making of this invention. In particular, the expression of myosin heavy chain detected by real-time PCR increases 10- to 100-fold when the cells are taken though three cycles of separation and reculturing over a 7 day period. A large proportion of the clusters in the composition exhibit spontaneous contractile activity: usually over 50%, and potentially between 80% and 100% when processed in the manner described.

Characterization of Cardiomyocyte Lineage Cells

The cells obtained according to the techniques of this invention can be characterized according to a number of phenotypic criteria. Cardiomyocytes and precursor cells derived from pPS cell lines often have morphological characteristics of cardiomyocytes from other sources. They can be spindle, round, triangular or multi-angular shaped, and they may show striations characteristic of sarcomeric structures detectable by immunostaining (Example 3). They may form myotube-like structures and show typical sarcomeres and atrial granules when examined by electron microscopy.

pPS derived cardiomyocytes and their precursors typically have at least one of the following cardiomyocyte specific markers:

Cardiac troponin I (cTnI), a subunit of troponin complex that provides a calcium-sensitive molecular switch for the regulation of striated muscle contraction.

Cardiac troponin T (cTnT)

Atrial natriuretic factor (ANF), a hormone expressed in developing heart and fetal cardiomyocytes but down-regulated in adults. It is considered a good marker for cardiomyocytes because it is expressed in a highly specific manner in cardiac cells but not skeletal myocytes.

The cells will also typically express at least one (and often at least 3, 5, or more) of the following markers:

sarcomeric myosin heavy chain (MHC)

Titin, tropomyosin, α-actinin, and desmin

GATA-4, a transcription factor that is highly expressed in cardiac mesoderm and persists in the developing heart. It regulates many cardiac genes and plays a role in cardiogenesis Nkx2.5, a cardiac transcription factor expressed in cardiac mesoderm during early mouse embryonic development, which persists in the developing heart.

MEF-2A, MEF-2B, MEF-2C, MEF-2D; transcription factors that are expressed in cardiac mesoderm and persist in developing heart N-cadherin, which mediates adhesion among cardiac cells Connexin 43, which forms the gap junction between cardiomyocytes.

β1-adrenoceptor (β1-AR)

creatine kinase MB (CK-MB) and myoglobin, which are elevated in serum following myocardial infarction Other markers that may be positive on cardiomyocytes and their precursors include α-cardiac actin, early growth response-I, and cyclin D2.

Tissue-specific markers can be detected using any suitable immunological technique—such as flow immunocytochemistry or affinity adsorption for cell-surface markers, immunocytochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be antibody-detectable if a significantly detectable amount of antibody will bind to the antigen in a standard immunocytochemistry or flow cytometry assay, optionally after fixation of the cells, and optionally using a labeled secondary antibody or other conjugate (such as a biotin-avidin conjugate) to amplify labeling.

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for details of general technique. Sequence data for other markers listed in this disclosure can be obtained from public databases such as GenBank. Expression at the mRNA level is said to be detectable according to one of the assays described in this disclosure if the performance of the assay on cell samples according to standard procedures in a typical controlled experiment results in clearly discernable hybridization or amplification product. Expression of tissue-specific markers as detected at the protein or mRNA revel is considered positive if the level is at least 2-fold, and preferably more than 10- or 50-fold above that of a control cell, such as art undifferentiated pPS cell or other unrelated cell type.

Once markers have been identified on the surface of cells of the desired phenotype, they can be used for immunoselection to further enrich the population by techniques such as immunopanning or antibody-mediated fluorescence-activated cell sorting.

Under appropriate circumstances, pPS-derived cardiomyocytes often show spontaneous periodic contractile activity. This means that when they are cultured in a suitable tissue culture environment with an appropriate $Ca^{++}$ concentration and electrolyte balance, the cells can be observed to contract across one axis of the cell, and then release from contraction, without having to add any additional components to the culture medium. The contractions are periodic, which means that they repeat on a regular or irregular basis, at a frequency between ~6 and 200 contractions per minute, and often between ~20 and ~90 contractions per minute (FIG. 5). Individual cells may show spontaneous periodic contractile activity on their own, or they may show spontaneous periodic contractile activity in concert with neighboring cells in a tissue, cell aggregate, or cultured cell mass.

The contractile activity of the cells can be characterized according to the influence of culture conditions on the nature and frequency of contractions. Compounds that reduce available $Ca^{++}$ concentration or otherwise interfere with transmembrane transport of $Ca^{++}$ often affect contractile activity. For example, the L-type calcium channel blocker diltiazem inhibits contractile activity in a dose-dependent manner (FIG. 5). On the other hand, adrenoceptor agonists like isoprenaline and phenylephrine have a positive chronotropic effect. Further characterization of functional properties of the cell can involve characterizing channels for $Na^+$, $K^+$, and $Ca^{++}$. Electrophysiology can be studied by patch clamp analysis for cardiomyocyte like action potentials. See Igelmund et al., Pflugers Arch. 437:669, 1999; Wobus et al., Ann. N.Y. Acad. Sci. 27:752, 1995; and Doevendans et al., J. Mol. Cell Cardiol. 32:839, 2000.

Functional attributes provide a manner of characterizing cells and their precursors in vitro, but may not be necessary for some of the applications referred to in this disclosure. For example, a mixed cell population enriched for cells bearing some of the markers listed above, but not all of the functional or electrophysiology properties, can be of considerable therapeutic benefit if they are capable of grafting to impaired cardiac tissue, and acquiring in vivo the functional properties needed to supplement cardiac function.

Where derived from an established line of pPS cells, the cell populations and isolated cells of this invention can be characterized as having the same genome as the line from which they are derived. This means that the chromosomal DNA will be over 90% identical between the pPS cells and the cardiac cells, which can be inferred if the cardiac cells are obtained from the undifferentiated line through the course of normal mitotic division. Cells that have been treated by recombinant methods to introduce a transgene (such as TERT) or knock out an endogenous gene are still considered to have the same genome as the line from which they are derived, since all non-manipulated genetic elements are preserved. Two cell populations can be shown to have essentially the same genome by standard techniques such as DNA fingerprinting. Alternatively, the relationship can be established by review of records kept during derivation of the cells. The characteristic that cardiomyocyte lineage cells are derived from the parent cell population is important in several respects. In particular, the undifferentiated cell population can be used for producing additional cells with a shared genome—either a further batch of cardiac cells, or another cell type that may be useful in therapy—such as a population that can pretolerize the patient to the histocompatibility type of the cardiac allograft.

For therapeutic use, it is often desirable that differentiated cell populations of this invention be substantially free of undifferentiated pPS cells. One way of depleting undifferentiated stem cells from the population is to transfect them with a vector in which an effector gene under control of a promoter that causes preferential expression in undifferentiated cells. Suitable promoters include the TERT promoter and the OCT-4 promoter. The effector gene may be directly lytic to the cell (encoding, for example, a toxin or a mediator of apoptosis). Alternatively, the effector gene may render the cell susceptible to toxic effects of an external agent, such as an antibody or a prodrug. Exemplary is a herpes simplex thymidine kinase (tk) gene, which causes cells in which it is expressed to be susceptible to ganciclovir. Suitable pTERT-tk constructs are provided in WO 98/14593 (Morin et al.).

Since it has now been demonstrated that cardiomyocytes and their precursors can be generated from pPS cells, it is well within the purview of the reader to adjust the differentiation paradigm illustrated in this disclosure to suit their own purposes. The reader can readily test the suitability of certain culture conditions, for example, by culturing pPS cells or their derivatives in the test conditions in parallel with cells obtained according to the illustrations in this disclosure and other control cell types (such as primary human cardiomyocytes, hepatocytes, or fibroblasts), and then comparing the phenotype of the cells obtained according to the markers listed above. Adjustment of culture and cell separation conditions to alter particular components is a matter of routine optimization normally expected for culture methods of this kind, and does not depart from the spirit of the claimed invention.

Genetic Alteration of Differentiated Cells

It may be desirable that the cells have the ability to replicate in certain drug screening and therapeutic applications, and to provide a reservoir for the generation of cardiomyocytes and their precursors. The cells of this invention can optionally be telomerized to increase their replication potential, either before or after they progress to restricted developmental lineage cells or terminally differentiated cells. pPS cells that are telomerized may be taken down the differentiation pathway described earlier; or differentiated cells can be telomerized directly.

Cells are telomerized by genetically altering them by transfection or transduction with a suitable vector, homologous recombination, or other appropriate technique, so that they express the telomerase catalytic component (TERT), typically under a heterologous promoter that increases telomerase expression beyond what occurs under the endogenous promoter. Particularly suitable is the catalytic component of human telomerase (hTERT), provided in International Patent Application WO 98/14592. For certain applications, species homologs like mouse TERT (WO 99/27113) can also be used.

Transfection and expression of telomerase in human cells is described in Bodnar et al., Science 279:349, 1998 and Jiang et al., Nat. Genet. 21:111, 1999. In another example, hTERT clones (WO 98/14592) are used as a source of hTERT encoding sequence, and spliced into an EcoRI site of a PBBS212 vector under control of the MPSV promoter, or into the EcoRI site of commercially available pBABE retrovirus vector, under control of the LTR promoter.

Differentiated or undifferentiated pPS cells are genetically altered using vector containing supernatants over a 8-16 h period, and then exchanged into growth medium for 1-2 days. Genetically altered cells are selected using a drug selection agent such as puromycin, G418, or blasticidin, and then recultured. They can then be assessed for hTERT expression by RT-PCR, telomerase activity (TRAP assay), immunocytochemical staining for hTERT, or replicative capacity. The following assay kits are available commercially for research purposes: TRAPeze® XL Telomerase Detection Kit (Cat. s7707; Intergen Co., Purchase N.Y.); and TeloTAGGG Telomerase PCR ELISAplus (Cat. 2,013,89; Roche Diagnostics, Indianapolis Ind.). TERT expression can also be evaluated at the mRNA by RT-PCR. Available commercially for research purposes is the LightCycler TeloTAGGG hTERT quantification kit (Cat. 3,012,344; Roche Diagnostics). Continuously replicating colonies will be enriched by further culturing under conditions that support proliferation, and cells with desirable phenotypes can optionally be cloned by limiting dilution.

In certain embodiments of this invention, pPS cells are differentiated into cardiomyocyte precursors, and then genetically altered to express TERT. In other embodiments of this invention, pPS cells are genetically altered to express TERT, and then differentiated into cardiomyocyte precursors or terminally differentiated cells. Successful modification to increase TERT expression can be determined by TRAP assay, or by determining whether the replicative capacity of the cells has improved.

Depending on the intended use of the cells, other methods of immortalization may also be acceptable, such as transforming the cells with DNA encoding myc, the SV40 large T antigen, or MOT-2 (U.S. Pat. No. 5,869,243, International Patent Applications WO 97/32972 and WO 01/23555). Transfection with oncogenes or oncovirus products is less suitable when the cells are to be used for therapeutic purposes. Telomerized cells are of particular interest in applications of this invention where it is advantageous to have cells that can proliferate and maintain their karyotype—for example, in pharmaceutical screening, and in therapeutic protocols where differentiated cells are administered to an individual in order to augment cardiac function.

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type. Of particular interest are cells that are genetically altered to express one or more growth factors of various types, cardiotropic factors such as atrial natriuretic factor, cripto, and cardiac transcription regulation factors, such as GATA-4, Nkx2.5, and MEF2-C. Production of these factors at the site of administration may facilitate adoption of the functional phenotype, enhance the beneficial effect of the administered cell, or increase proliferation or activity of host cells neighboring the treatment site.

Use of Cardiomyocytes and Their Precursors

This invention provides a method to produce large numbers of cells of the cardiomyocyte lineage. These cell populations can be used for a number of important research, development, and commercial purposes.

The cells of this invention can be used to prepare a cDNA library relatively uncontaminated with cDNA preferentially expressed in cells from other lineages. For example, cardiomyocytes are collected by centrifugation at 1000 rpm for 5 min, and then mRNA is prepared from the pellet by standard techniques (Sambrook et al., supra). After reverse transcribing into cDNA, the preparation can be subtracted with cDNA from undifferentiated pPS cells, other progenitor cells, or end-stage cells from the cardiomyocyte or any other developmental pathway.

The differentiated cells of this invention can also be used to prepare antibodies that are specific for markers of cardiomyocytes and their precursors. Polyclonal antibodies can be prepared by injecting a vertebrate animal with cells of this invention in an immunogenic form. Production of monoclonal antibodies is described in such standard references as U.S. Pat. Nos. 4,491,632, 4,472,500 and 4,444,887, and Methods in Enzymology 73B:3 (1981). Specific antibody molecules can also be produced by contacting a library of immunocompetent cells or viral particles with the target antigen, and growing out positively selected clones. See Marks et al., New Eng. J. Med. 335:730, 1996, and McGuiness et al., Nature Biotechnol. 14:1449, 1996. A further alternative is reassembly of random DNA fragments into antibody encoding regions, as described in EP patent application 1,094,108 A.

By positively selecting using the specific cells of this invention, and negatively selecting using cells bearing more broadly distributed antigens (such as embryonic cell progeny with other phenotypes) or adult-derived cardiomyocytes, the desired specificity can be obtained. The antibodies in turn can be used to identify or rescue heart cells of a desired phenotype from a mixed cell population, for purposes such as costaining during immunodiagnosis using tissue samples, and isolating precursor cells from terminally differentiated cardiomyocytes and cells of other lineages.

The cells of this invention are also of interest in identifying expression patterns of transcripts and newly synthesized proteins that are characteristic for cardiomyocytes, and may assist in directing the differentiation pathway or facilitating interaction between cells. Expression patterns of the differentiated cells are obtained and compared with control cell lines, such as undifferentiated pPS cells, other types of committed precursor cells (such as pPS cells differentiated towards other lineages), or terminally differentiated cells.

The use of microarray in analyzing gene expression is reviewed generally by Fritz et al Science 288:316, 2000; *Microarray Biochip Technology*, L Shi, at the Gene-Chips website. An exemplary method is conducted using a Genetic Microsystems array generator, and an Axon GenePix™ Scanner. Microarrays are prepared by first amplifying cDNA fragments encoding marker sequences to be analyzed, and spotted directly onto glass slides To compare mRNA preparations from two cells of interest, one preparation is converted into Cy3-labeled cDNA, while the other is converted into Cy5-labeled cDNA. The two cDNA preparations are hybridized simultaneously to the microarray slide, and then washed to eliminate non-specific binding. The slide is then scanned at wavelengths appropriate for each of the labels, the resulting fluorescence is quantified, and the results are formatted to give an indication of the relative abundance of mRNA for each marker on the array.

Drug Screening

Cardiomyocytes of this invention can be used to screen for factors (such as solvents, small molecule drugs, peptides, oligonucleotides) or environmental conditions (such as culture conditions or manipulation) that affect the characteristics of such cells and their various progeny.

In some applications, pPS cells (undifferentiated or differentiated) are used to screen factors that promote maturation into later-stage cardiomyocyte precursors, or terminally differentiated cells, or to promote proliferation and maintenance of such cells in long-term culture. For example, candidate maturation factors or growth factors are tested by adding them to cells in different wells, and then determining any phenotypic change that results, according to desirable criteria for further culture and use of the cells.

Other screening applications of this invention relate to the testing of pharmaceutical compounds for their effect on cardiac muscle tissue maintenance or repair. Screening may be done either because the compound is designed to have a pharmacological effect on the cells, or because a compound designed to have effects elsewhere may have unintended side effects on cells of this tissue type. The screening can be conducted using any of the precursor cells or terminally differentiated cells of the invention.

The reader is referred generally to the standard textbook *In vitro Methods in Pharmaceutical Research*, Academic Press, 1997, and U.S. Pat. No. 5,030,015. Assessment of the activity of candidate pharmaceutical compounds generally involves combining the differentiated cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in *In vitro Methods in Pharmaceutical Research*, Academic Press, 1997) for further elaboration.

Effect of cell function can be assessed using any standard assay to observe phenotype or activity of cardiomyocytes, such as marker expression, receptor binding, contractile activity, or electrophysiology—either in cell culture or in vivo. Pharmaceutical candidates can also be tested for their effect on contractile activity—such as whether they increase or decrease the extent or frequency of contraction. Where an effect is observed, the concentration of the compound can be titrated to determine the median effective dose ($ED_{50}$).

Animal Testing

This invention also provides for the use of cardiomyocytes and their precursors to enhance tissue maintenance or repair of cardiac muscle for any perceived need, such as an inborn error in metabolic function, the effect of a disease condition, or the result of significant trauma.

To determine the suitability of cell compositions for therapeutic administration, the cells can first be tested in a suitable animal model. At one level, cells are assessed for their ability to survive and maintain their phenotype in vivo. Cell compositions are administered to immunodeficient animals (such as nude mice, or animals rendered immunodeficient chemically or by irradiation). Tissues are harvested after a period of regrowth, and assessed as to whether pPS derived cells are still present.

This can be performed by administering cells that express a detectable label (such as green fluorescent protein, or β-galactosidase); that have been prelabeled (for example, with BrdU or [$^3$H]thymidine), or by subsequent detection of a constitutive cell marker (for example, using human-specific antibody). The presence and phenotype of the administered cells can be assessed by immunohistochemistry or ELISA using human-specific antibody, or by RT-PCR analysis using primers and hybridization conditions that cause amplification to be specific for human polynucleotides, according to published sequence data.

Suitability can also be determined by assessing the degree of cardiac recuperation that ensues from treatment with a cell population of pPS-derived cardiomyocytes. A number of animal models are available for such testing. For example, hearts can be cryoinjured by placing a precooled aluminum rod in contact with the surface of the anterior left ventricle wall (Murry et al., J. Clin. Invest. 98:2209, 1996; Reinecke et al., Circulation 100:193, 1999; U.S. Pat. No. 6,099,832; Reinecke et al., Circ Res., Epub March 2004). In larger animals, cryoinjury can be infarcted by placing a 30-50 mm copper disk probe cooled in liquid $N_2$ on the anterior wall of the left ventricle for ~20 min (Chiu et al., Ann. Thorac. Surg. 60:12, 1995). Infarction can be induced by ligating the left main coronary artery (Li et al., J. Clin. Invest. 100:1991, 1997). Injured sites are treated with cell preparations of this invention, and the heart tissue is examined by histology for the presence of the cells in the damaged area. Cardiac function can be monitored by determining such parameters as left ventricular end-diastolic pressure, developed pressure, rate of pressure rise, and rate of pressure decay.

Therapeutic Use in Humans

After adequate testing, differentiated cells of this invention can be used for tissue reconstitution or regeneration in a human patient or other subject in need of such treatment. The cells are administered in a manner that permits them to graft or migrate to the intended tissue site and reconstitute or regenerate the functionally deficient area. Special devices are available that are adapted for administering cells capable of reconstituting cardiac function directly to the chambers of the heart, the pericardium, or the interior of the cardiac muscle at the desired location.

Where desirable, the patient receiving an allograft of pPS derived cardiomyocytes can be treated to reduce immune rejection of the transplanted cells. Methods contemplated include the administration of traditional immunosuppressive drugs like cyclosporin A (Dunn et al., Drugs 61:1957, 2001), or inducing immunotolerance using a matched population of pPS derived cells (WO 02/44343; U.S. Pat. No. 6,280,718; WO 03/050251). Another approach is to adapt the cardiomyocyte cell population to decrease the amount of uric acid produced by the cells upon transplantation into a subject, for example, by treating them with allopurinol. Alternatively or in conjunction, the patient is prepared by administering allopurinol, or an enzyme that metabolizes uric acid, such as urate oxidase. This is further described in U.S. patent application 60/532,700, filed Dec. 23, 2003.

Patients suitable for receiving regenerative medicine according to this invention include those having acute and chronic heart conditions of various kinds, such as coronary heart disease, cardiomyopathy, endocarditis, congenital cardiovascular defects, and congestive heart failure. Efficacy of treatment can be monitored by clinically accepted criteria, such as reduction in area occupied by scar tissue or revascularization of scar tissue, and in the frequency and severity of angina; or an improvement in developed pressure, systolic pressure, end diastolic pressure, Δpressure/Δtime, patient mobility, and quality of life.

The cardiomyocytes of this invention can be supplied in the form of a pharmaceutical composition, comprising an isotonic excipient prepared under sufficiently sterile conditions for human administration. When the differentiation procedure has involved culturing the cells as Cardiac Bodies™, it may be desirable to disperse the cells using a protease or by gentle mechanical manipulation into a suspension of single cells or smaller clusters. To reduce the risk of cell death upon engraftment, the cells may be treated by heat shock or cultured with ~0.5 U/mL erythropoietin ~24 hours before administration.

For general principles in medicinal formulation, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cardiomyocytes. Suitable ingredients include matrix proteins that support or promote adhesion of the cardiomyocytes, or complementary cell types, especially endothelial cells.

This invention also includes a reagent system, comprising a set or combination of cells that exist at any time during manufacture, distribution, or use. The cell sets comprise any combination of two or more cell populations described in this disclosure, exemplified but not limited to a type of differentiated pPS-derived cell (cardiomyocytes, cardiomyocyte precursors, Cardiac Bodies™, and so on), in combination with undifferentiated pPS cells or other differentiated cell types, sometimes sharing the same genome. Each cell type in the set may be packaged together, or in separate containers in the same facility, or at different locations, at the same or different times, under control of the same entity or different entities sharing a business relationship.

Pharmaceutical compositions of this invention may optionally be packaged in a suitable container with written instructions for a desired purpose, such as the reconstitution of cardiomyocyte cell function to improve some abnormality of the cardiac muscle.

The following examples are provided as further non-limiting illustrations of particular embodiments of the invention.

EXAMPLES

Example 1

Feeder-Free Propagation of Embryonic Stem Cells

Established lines of undifferentiated human embryonic stem (hES) cells were maintained in a culture environment essentially free of feeder cells.

Feeder-free cultures were maintained using conditioned medium prepared using primary mouse embryonic fibroblasts isolated according to standard procedures (WO 01/51616). Fibroblasts were harvested from T150 flasks by washing once with $Ca^{++}/Mg^{++}$ free PBS and incubating in 1.5-2 mL trypsin/EDTA (Gibco) for ~5 min. After the fibroblasts detached from the flask, they were collected in mEF media (DMEM+10% FBS). The cells were irradiated at 4000 rad, counted and seeded at ~55,000 cells $cm^2$ in mEF medium (525,000 cells/well of a 6 well plate).

After at least 4 h, the medium were exchanged with SR containing ES medium (80% knockout DMEM (Gibco BRL, Rockville Md.), 20% knockout serum replacement (Gibco), 1% Non-essential amino acids (Gibco), 1 mM L-glutamine (Gibco), 0.1 mM β-mercaptoethanol (Sigma, St. Louis, Mo.), supplemented with 4 ng/mL recombinant human basic fibroblast growth factor (bFGF; Gibco). About 0.3-0.4 mL of medium was conditioned per $cm^2$ of plate surface area. Before addition to the hES cultures, the conditioned medium was supplemented with 4 ng/mL of human bFGF.

Plates for culturing the hES cells were coated with Matrigel® (Becton-Dickinson, Bedford Mass.) by diluting stock solution ~1:30 in cold KO DMEM, dispensing at 0.75-1.0 mL per 9.6 $cm^2$ well, and incubating for 1-4 h at room temp or overnight at 4° C.

hES cultures were passaged by incubation in ~200 U/mL collagenase IV for about 5'-10 minutes at 37° C. Cells were harvested by scraping followed by gentle dissociation into small clusters in conditioned medium, and then seeded onto Matrigel® coated plates. About one week after seeding the cultures became confluent and could be passaged. Cultures maintained under these conditions for over 180 days continued to display ES-like morphology.

Immunocytochemistry was performed by incubating samples with primary antibody for SSEA-4 (1:20), Tra-1-60 (1:40) and Tra-1-81 (1:80), diluted in knockout DMEM at 37° C. for 30 min. The cells were washed with warm knockout DMEM and fixed in 2% paraformaldehyde for 15 min, and then washed with PBS. The cells were incubated with 5% goat serum in PBS at room temp for 30 min, followed by the FITC-conjugated goat anti-mouse IgG (1:125) (Sigma) for 30 min. Cells were washed, stained with DAPI and mounted.

Cells were also examined for expression of alkaline phosphatase, a marker for undifferentiated ES cells. This was performed by culturing the cells on chamber slides, fixing with 4% paraformaldehyde for 15 min, and then washing with PBS. Cells were then incubated with alkaline phosphatase substrate (Vector Laboratories, Inc., Burlingame, Calif.) at room temperature in the dark for 1 h. Slides were rinsed for 2-5 min in 100% ethanol before mounting.

FIG. 1 shows marker expression on the hES cells detected by histochemistry. SSEA-4, Tra-1-60, Tra-1-81, and alkaline phosphatase were expressed by the hES colonies, as seen for the cells on feeders—but not by the differentiated cells in between the colonies.

Expression of the undifferentiated hES cell markers was assayed by reverse-transcriptase PCR amplification. For radioactive relative quantification of individual gene products, QuantumRNA™ Alternate18S Internal Standard primers (Ambion, Austin Tex., USA) were employed according to the manufacturer's instructions. Briefly, the linear range of amplification of a particular primer pair was determined, then coamplified with the appropriate mixture of alternate 18S primers:competimers to yield PCR products with coinciding linear ranges. Before addition of AmpliTaq™ (Roche) to PCR reactions, the enzyme was pre-incubated with the TaqStart™ antibody (ProMega) according to manufacturer's instructions. Radioactive PCR reactions were analyzed on 5% non-denaturing polyacrylamide gels, dried, and exposed to phosphoimage screens (Molecular Dynamics) for 1 hour.

Screens were scanned with a Molecular Dynamics Storm 860 and band intensities were quantified using ImageQuant™ software. Results are expressed as the ratio of radioactivity incorporated into the hTERT or Oct-4 band, standardized to the radioactivity incorporated into the 18s band. Primer sequences used in this experiment can be found in International patent publication WO 01/51616.

The transcription factor Oct-4 is normally expressed in the undifferentiated hES cells and is down-regulated upon differentiation. Cells maintained on Matrigel® in conditioned medium expressed hTERT and Oct-4. Telomerase activity was measured by TRAP assay (Kim et al., Science 266:2011, 1997; Weinrich et al., Nature Genetics 17:498, 1997). Cells maintained in the feeder-free culture environment showed positive telomerase activity after over 180 days in culture.

Pluripotency of the undifferentiated cells cultured without feeders was determined by forming embryoid bodies in suspension culture for 4 days, and then culturing on poly-ornithine coated plates for 7 days. Immunocytochemistry showed staining patterns consistent with cells of the neuron and cardiomyocyte lineages, and cells staining for α-fetoprotein, a marker of endoderm lineage. The undifferentiated cells were also tested for their ability to form teratomas by intramuscular injection into SCID mice. Resulting tumors were excised after 78-84 days. Cell types from all three germ layers were identified by histological analysis.

Example 2

Differentiation of hES Cells to Cardiomyocytes hES cell lines, H1, H7, H9, and H9.2 (a cloned line derived from H9) were initially maintained on feeder cells and later under feeder-free conditions, as in Example 1. Cultures were passaged weekly by incubation in 200 U/mL collagenase IV for ~5-10 minutes at 37° C., dissociated, and then seeded at a 1:3 to 1:6 ratio, ~90,000-170,000 cells/cm$^2$, onto Matrigel®-coated plates and maintained in medium conditioned by primary mouse embryonic fibroblasts.

FIG. 2 (Upper Panel) shows the scheme for differentiating hES cells into cardiomyocytes. Differentiation was initiated by culturing hES cells in suspension to form embryoid bodies. hES cells were dissociated into small clumps by incubating in 1 mg/ml collagenase IV at 37° C. for ~5-10 min, and then cultured in suspension in differentiation medium to form aggregates. The differentiation medium contained 80% knockout Dulbecco's modified Eagle's medium (KO-DMEM) (Gibco BRL, Rockville, Md.), 1 mM L-glutamine, 0.1 mM β-mercaptoethanol and 1% nonessential amino acids stock (Gibco BRL, Rockville, Md.), supplemented with 20% fetal bovine serum.

After 4 days in suspension culture, embryoid bodies were transferred to gelatin-coated plates or chamber slides. The EBs attached to the surface after seeding, proliferated and differentiated into a heterogeneous cell population. Spontaneously contracting cells were observed in various regions of the culture at differentiation day 8.

FIG. 2 (Lower Panel) shows that as cells continue to differentiate, the proportion of plated embryoid bodies containing beating cells increases. Contracting cells could be found in the long-term cultures as late as day 32.

Beating cardiomyocytes were isolated from EB outgrowth mechanically at differentiation day 11-14, collected into a 15-mL tube containing the low-calcium medium or PBS, and then washed. Different agents were tested for their ability to generate single-cell suspensions of viable cardiomyocytes, including trypsin, EDTA, collagenase IV or collagenase B. Viable contracting single cardiomyocytes were obtained using cells incubated in collagenase B solution at 37° C. for 60-120 min depending on the collagenase activity. Cells were then resuspended in KB medium (85 mM KCl, 30 mM $K_2HPO_4$, 5 mM $MgSO_4$, 1 mM EGTA, 5 mM creatine, 20 mM glucose, 2 mM $Na_2ATP$, 5 mM pyruvate, and 20 mM taurine, buffered to pH 7.2) (Maltsev et al., Circ. Res. 75:233, 1994). The cells are incubated in the medium at 37° C. for 15-30 min, dissociated, and then seeded into chamber slides and cultured in differentiation medium. Upon subculture, single cardiomyocytes survived and continued to beat.

All hES cell lines tested, including H1, H7, H9, H9.1, and H9.2, have the potential to generate beating cardiomyocytes, even after being maintained for over 50 passages (~260 population doublings).

Example 3

Characterization of Cardiomyocytes hES-derived cells prepared as in Example 2 were analyzed for the presence of phenotypic markers characteristic of cardiomyocytes.

Immunostaining of EB outgrowth cultures or dissociated cardiomyocytes was performed as follows. Differentiated cultures were fixed in methanol/acetone (3:1) at −20° C. for 20 min. Cells were then washed 2× with PBS, blocked with 5% normal goat serum (NGS) in PBS at 4° C. overnight, followed by incubation at RT for 2 h with primary antibody diluted 1:20 to 1:800 in primary antibody diluting buffer (Biomeda Corp., Foster City Calif.) or 1% NGS in PBS. After washing, cells were incubated with the corresponding FITC or Texas Red™-conjugated secondary antibody diluted in 1% NGS in PBS at RT for 30-60 min. Cells were washed again, stained with DAPI and mounted with Vectashield™ (Vector Laboratories Inc., Burlingame Calif.). Photomicroscopy was performed on a Nikon Iabphot™ equipped with epifluorescence and a SPOT CCD cooled camera.

Individual contracting foci in differentiated cultures of H9.2 cells were photographed at day 15 to record the contracting areas before the culture was fixed. The culture was then stained for cardiac troponin I (cTnI), and matched to the light micrographs to determine the percentage of contracting areas that were positive for cTnI staining. 100% of the contracting areas stained positive for cTnI, while there was almost no staining observed in non-beating cells.

Western blotting for cTnI expression was conducted as follows. Undifferentiated cells and differentiated cells were dissolved in lysis buffer, separated by 10% SDS-PAGE and then transferred onto nitrocellulose membranes (Schleicher & Schuell). The membranes were blocked with 5% non-fat dry milk in PBS supplemented with 0.05% Tween™ 20 (PBST) at RT for 1 h and incubated with monoclonal antibody against cTnI diluted 1:2000 with 1% non-fat dry milk in PBST at 4° C. overnight. The blots were then incubated with horse anti-mouse IgG (H+L) antibody conjugated with horseradish peroxidase (Vector Laboratories Inc., Burlingame Calif.) diluted 1:8000 with 1% non-fat dry milk in PBST at RT for 1.5 h. Signals for the binding of the antibody were detected by SuperSignal™ West Pico chemiluminescence system (Pierce, Rockford, Ind.). As a control, β-actin was probed on the same blot as follows: The blot was washed in PBS after the first ECL detection, exposed to the Vector™-SG substrate for about 5 min (Vector Laboratories Inc., Burlingame, Calif.) and then reprobed with monoclonal antibody against β-actin (Sigma).

FIG. 3 (Upper Panel) shows the results of Western blot analysis. There is a band at ~31 kDa (corresponding in size to human cTnI) for wells containing contracting cells (lane 2 and 3) but not for undifferentiated hES cells (lane 1) or wells containing no contracting cells (lane 4). All lanes stained for the presence of β-actin (a standard for protein recovery).

Real time reverse transcription PCR was performed with LightCycler. For relative quantification of αMHC, RNA samples and primers were mixed with RT-PCR reaction mixture (LightCycler RNA Amplification Kit-Hybridization Probes, Roche Molecular Biochemicals) following the kit directions. The reaction conditions are following: RT at 55° C. for 10 min; denaturation at 95° C. for 30 sec; amplification for 45 cycles at 95° C. for 0 sec, 60° C. for 15 sec and 72° C. for 13 sec. The reactions were analyzed using LightCycler 3 program. Relative MHC levels were represented as ratio of MHC and 28S from triplicate reactions for each sample.

FIG. 3 (Lower Panel) shows the results. The level of αMHC increased significantly after day 7 of differentiation, but was undetectable in undifferentiated hES cells or early stages of differentiated cells. The expression levels continued to increase at later times, in parallel with the appearance of beating cells. The expression of hTERT was found to decrease during differentiation.

Collagenase B was used to dissociate hES-derived cardiomyocytes into single cells as described in Example 2. The dissociated cardiomyocytes were examined for expression of sarcomeric myosin heavy chain (MHC), titin, tropomyosin, α-actinin, desmin, cTnI and cardiac troponin T (cTnT).

FIG. 4 shows the results. Single cells and clusters stained positive for all these markers. The stained single cardiomyocytes were spindle, round and tri- or multi-angular shaped. The striations characteristic of the sarcomeric structures is also seen, consistent with the contractile apparatus necessary for muscle function.

GATA-4 is a transcription factor that is highly expressed in cardiac mesoderm. Strong GATA-4 immunoreactivity was observed in all nuclei of cTnI-positive cells. Western blots indicate that GATA-4 was strongly expressed in differentiated hES cells containing contracting cells (FIG. 1, lane 2 and 3) but was not detectable in differentiated culture with no evidence of contracting cells (FIG. 1, lane 4). A weak signal was also detected in undifferentiated cells (lane 1). This may be due to spontaneous differentiation to visceral endoderm, which also expresses GATA-4, or to low-level expression of GATA-4 by the undifferentiated cells themselves.

The MEF2 cardiac transcription factors were detected by immunocytochemistry in all nuclei of the cTnI-positive cells. A semiquantitative RT-PCR for the cardiac transcription factor Nkx2.5 (Xu et al., Dev Biol. 196:237, 1998) indicated that it was highly expressed in cultures containing beating cardiomyocytes, but undetectable in undifferentiated cells. Positive signals for adhesion marker N-cadherin and gap junction marker connexin 43 were detected in between cardiac cells identified by cTnI or MHC expression, but not in surrounding non-cardiac cells. In addition, we stained the partially dissociated cells with antibody against β1-adrenoceptor (β1-AR) and cTnI. Specific staining of surface markers indicates that the cells can be further enriched by a sorting technique based on these markers.

Creatine kinase MB (CK-MB) and myoglobin were also detected by immunostaining of the hES-derived cardiomyocytes, costaining with MHC. CK-MB is thought to be responsible for high-energy storage, and is mostly restricted to cells of the myocyte lineage. Myoglobin is a cytosolic oxygen binding protein responsible for storage and diffusion of $O_2$ within myocytes. Both CK-MB and myoglobin are commonly used to diagnose acute myocardial infarction. Strong immunoreactivity for β1-adrenoceptor (β1-AR) was observed on cTnI-positive cells.

Atrial natriuretic factor (ANF) was upregulated during cardiac differentiation of hES cells as detected by a semiquantitative RT-PCR. 18% of the cTnI positive cells doublestained for Ki-67—a protein present in actively dividing cells but not in resting G0 cells—showing that the cells still have the capacity to proliferate.

Taken together, these data indicate that hES-derived cardiomyocytes have appropriate gene expression patterns consistent with the phenotype of early stage (fetal) cardiomyocytes.

Example 4

Enrichment of Cardiomyocytes by Density Centrifugation

Cardiomyocytes were further enriched by density separation on a discontinuous gradient of Percoll™ (a density separation medium comprising colloidal PVP-coated silica). Cardiomyocytes were generated by induction of hES differentiation in suspension for 4 days and further differentiated on gelatin-coated plates for 15 days. The cells were dissociated with collagenase B at 37° C. for 2 hr. Cells were washed and resuspended in the differentiation medium. After settling for 5 min, the cell suspension was loaded onto a layer of 40.5% Percoll™ (Pharmacia) (~1.05 g/mL) overtop of a layer of 58.5% Percoll™ (~1.075 g/mL). The cells were then centrifuged at 1500 g for 30 min. After centrifugation, cells on top of the Percoll™ (fraction I) and a layer of cells in the interface of two layers of Percoll™ (fraction II) were collected. The collected cells were washed, resuspended in the differentiation medium, and seeded at $10^4$ per well into chamber slides.

After one week, cells were fixed and stained for expression of myosin heavy chain (MHC) (Example 3). Percentage of MHC positive cells was determined by counting cells in 30 images from triplicate wells for each fraction and presented as mean±standard deviation of cells from 3 wells). Beating cells were observed in both fractions, but fraction II contained more. Results are shown in Table 1. The enrichment attained in Fraction II was at least ~20-fold higher than the starting cell population (this corresponds to what is indicated as Fraction III in subsequent examples).

TABLE 1

Percoll ™ Separation of hES-derived Cardiomyocytes

| Fraction | Cell Count | Proliferation | Beating Cells | % staining for MHC |
|---|---|---|---|---|
| I | $1.92 \times 10^6$ | +++ | + | 2.7 ± 3.3% |
| II | $0.56 \times 10^6$ | + | ++ | 26.8 ± 4.1% |

Example 5

Pharmacological Responses

The function of hES-derived cardiomyocytes was tested by determining whether the cardiomyocytes respond appropriately to the chronotropic effects of cardioactive drugs.

Studies of Pharmacological Response

EBs were plated on to gelatin-coated 24-well plates and allowed to differentiate, as in Example 2. Contracting cardiomyocytes at differentiation day 15-21 were used for examining pharmacological response. The frequency of the spontaneous beating was measured by counting the contraction rate of the beating areas maintained in the differentiation medium in a 37° C. heating chamber of an inverted microscope. The cells were then incubated with test compounds in the incubator for 20-30 min, and observed for contraction rate. Dose-dependent effects were determined by cumulatively applying of increasing concentrations of each substrate. Data represent the mean pulsation rate±standard error of the mean measured on 10-20 beating areas.

To demonstrate these cells express functional L-type calcium channel that plays a critical role in cardiac contractile function, we examined the effect of the L-type calcium channel blocker diltiazem on the beating of hES-derived cardiomyocytes. Differentiated cells were incubated with various concentrations of the drug and the number of beats per minute was counted. The cells were then washed with medium, maintained in differentiation medium for 24 h and observed for the time taken to recover contractility.

FIG. 5 (Panel A) shows that the beating rate was inhibited by diltiazem in a concentration-dependent manner. When cells were treated with $10^{-5}$ M diltiazem, 100% of the beating areas stopped contraction. The contraction recovered to normal levels 24-48 h after removal of the drugs. Each data point represents the mean±standard error of the mean pulsation rate. Statistical significance was tested by the Fisher's PLSD test: $*p<0.05$, $p<0.005$, $*p<0.0005$. This observation shows that the hES-derived cardio-myocytes have functional L-type calcium channels. In a separate experiment, clenbuterol was found to increase the beating rate for cells taken at Day 72 from about 72 beats/min to about 98 beats/min (1-10 nM, $p<0.005$).

Panels B and C show that there are positive chronotropic effects induced by isoprenaline (a β-adrenoceptor agonist) and phenylephrine (an α-adrenoceptor agonist). Panels D and E show that the phosphodiesterase inhibitor IBMX and the β2-adrenoceptor agonist clenbuterol have a similar effect. Thus, the hES cell derived cells respond to cardioactive drugs in a manner appropriate for cells of the cardiomyocyte lineage.

Example 6

Cardiotropic Factors as Differentiation Induction Agents hES cells of the H1 or H9 line being cultured as embryoid bodies were treated at differentiation day 1-4, 4-6 or 6-8 with 5-aza-deoxy-cytidine, a cytosine analog that affects DNA methylation, thereby activating gene expression. Cells were harvested at day 15, and analyzed for cardiac α-MHC by real-time RT-PCR.

The RT-PCR assay from Example 3 was adapted for the Taqman™ 7700 sequence detection system using the same primers, amplifying for 40 cycles at 95° C. for 15 sec and 60° C. for 1 min. 18S ribosomal RNA was amplified for a control using a kit for Taqman™ ribosomal RNA control reagents (Applied Biosystems). Reactions were analyzed by ABI Prism™ 7700 Sequence Detection system.

FIG. 6 shows the results of using 5-aza-deoxy-cytidine as a differentiation induction agent (mean±S.D., ratio of αMHC to 18S RNA for determinations in triplicate). The data show that 1 to 10 μM of 5-aza-deoxy-cytidine at day 6-8 significantly increased the expression of cardiac α-MHC, correlating with an increased proportion of beating areas in the culture.

Other reagents examined for an ability to induce cardiomyocyte differentiation included dimethyl sulfoxide (DMSO) and all-trans retinoic acid (RA). Embryoid bodies treated with 0.5% DMSO from days 0-4 produced fewer beating areas than non-treated cultures. Beating cells were absent from cultures treated with 0.8% or 1% DMSO, and 1.5% DMSO was actually toxic to the cells. DMSO treatment also caused significant reduction in α-MHC expression, compared with untreated cultures.

Retinoic acid was applied to differentiating hES cultures at doses between $10^{-9}$ and $10^{-5}$ M. At day 0-4, the RA was toxic to the cells, while at days 4-8, 8-15, or 4-15, there was no increase in beating cells compared with untreated cultures.

Thus, 5-aza-deoxy-cytidine was an effective cardiomyocyte differentiation inducer, increasing the proportion of cardiomyocyte cells in the population. In contrast, DMSO and retinoic acid inhibit cardiomyocyte differentiation, even though these compounds generate cardiomyocytes from embryonic carcinoma or embryonic stem cells (Wobus et al., J. Mol. Cell Cardiol. 29:1525, 1997; McBurney et al., Nature 299:165, 1982).

Cardiomyocyte differentiation was also achieved in a direct differentiation paradigm. Undifferentiated hES cells of the H7 line were dissociated and plated directly onto gelatin-coated plates without going through an embryoid body stage. The plated cells were cultured in differentiation medium (80% KO-DMEM, 1 mM L-glutamine, 0.1 mM β-mercaptoethanol, 1% amino acids, and 20% fetal bovine serum). Contracting cardiomyocytes were found at day 18 in cultures treated with 10 μM 5-aza-deoxy-cytidine at day 10-12 or 12-14, and at later times in all cultures.

Example 7

Effective Combinations of Cardiotropic Factors

This example is an investigation of combined effects of added growth factors and 5-aza-deoxy-cytidine to influence cardiomyocyte differentiation of human ES cells.

The human ES cell line designated H1 routinely yields fewer beating cardiomyocytes than the H7 or H9 lines after the standard embryoid body protocol. In order to increase the yield of cardiomyocytes, a series of growth factors as well as 5-aza-deoxy-cytidine were added to differentiating H1 cultures.

The rationale was as follows. Group I factors were selected as being able to supply functions of the hypoblast during initial commitment. Group II factors were selected as able to supply functions of endoderm during subsequent development in combination with Group I factors. Group III factors were selected as survival factors for cardiomyocytes in extended culture. A typical working concentration was defined as "medium" level, with 4-fold lower and 4-fold higher levels defined as "low" and "high" levels. The concentrations are shown below:

TABLE 2

Exemplary Cardiotropic Factors

| Growth Factor | Low concentration. | Medium concentration. | High concentration. |
|---|---|---|---|
| Group I | | | |
| Activin A | 6.25 ng/mL | 25 ng/mL | 100 ng/mL |
| TGF β1 | 2.5 ng/mL | 10 ng/mL | 40 ng/mL |
| IGF II | 6.25 nM | 25 nM | 100 nM |

TABLE 2-continued

Exemplary Cardiotropic Factors

| Growth Factor | Low concentration. | Medium concentration. | High concentration. |
|---|---|---|---|
| Group II | | | |
| BMP 4 | 1.25 ng/mL | 5 ng/mL | 20 ng/mL |
| FGF 4 | 12.5 ng/mL | 50 ng/mL | 200 ng/mL |
| Insulin | 6.25 ng/mL | 25 ng/mL | 100 ng/mL |
| bFGF | 12.5 ng/mL | 50 ng/mL | 200 ng/mL |
| PDGF-BB | 12.5 ng/mL | 50 ng/mL | 200 ng/mL |
| 5-aza-deoxy-cytidine | 10 µM | 10 µM | 10 µM |
| Group III | | | |
| IGF I | 6.25 nM | 25 nM | 100 nM |
| IGF II | 6.25 nM | 25 nM | 100 nM |
| LIF | 5 ng/mL | 20 ng/mL | 80 ng/mL |
| EGF | 6.25 ng/mL | 25 ng/mL | 100 ng/mL |
| PDGF-BB | 0.9 ng/mL | 3.6 ng/mL | 14.4 ng/mL |
| bFGF | 2.5 ng/mL | 10 ng/mL | 40 ng/mL |
| Insulin | 6.25 nM | 25 nM | 100 nM |

FIG. 7 (Upper Panel) shows the scheme for use of these factors. H1 cells at passage 48 were used to generate embryoid bodies by collagenase treatment followed by mechanically dislodging the cells from the dish by scraping with a 5 mL pipet. The contents of one 10 cm$^2$ well of cells was transferred to a single 10 cm$^2$ well of a low adherence plate and cultured in 4 ml of DMEM plus 20% FBS in the presence or absence of additional factors for 4 days. At the end of day 4, each suspension of embryoid bodies was divided into 2 aliquots plated in 2 wells of a gelatin-coated adherent 6 well tissue culture plate (10 cm$^2$/well). The adherent embryoid bodies and their outgrowths were cultured in 4 mL of DMEM plus 20% FBS in the presence or absence of additional factors for 11 days, after which the number of beating regions in each well was observed by light microscopy, and RNA was harvested from each well for subsequent quantitative PCR analysis.

Group I factors were added on day 0, (the day on which undifferentiated cells were transferred to suspension culture to generate embryoid bodies) and were present continuously until day 8 (4 days after the embryoid bodies were plated in gelatin-coated wells). Group II factors were added on day 4 (at the time of plating) and were present continuously until day 8. Group III factors were added on day 8 and were present continuously until the end of the experiment (day 15). A subset of cultures was exposed to 5-aza-deoxy-cytidine for 48 hrs (day 6-8). Cultures were re-fed with fresh media plus or minus factors on days 6, 8, 11, and 13.

It was observed that while no beating regions were observed in the control cultures (those maintained in the absence of supplementary factors/5-aza-deoxy-cytidine) or those maintained in the presence of the growth factors in the absence of 5-aza-deoxy-cytidine, beating areas were observed in all wells receiving the combination of growth factors plus 5-aza-deoxy-cytidine.

FIG. 7 (Lower Panel) shows quantitative PCR analysis (Taqman™) for expression of the cardiac gene a myosin heavy chain (αMHC), relative to the level in normal heart RNA. The level of expression was significantly higher in cells exposed to growth factors (GF) plus 5-aza-deoxy-cytidine. The lowest concentrations tested were sufficient to achieve higher αMHC expression (30-fold higher than the levels seen in control.

These results were elaborated in a subsequent experiment. H1 cells (passage 38) were cultured as before, except that: a) only the lowest concentrations of factors used in the previous experiment were employed; and b) in one set of samples, the Group III treatment was omitted. Level of marker expression was then determined in real-time PCR assay relative to undifferentiated cells.

FIG. 8 shows that omission of Group III from the protocol led to a further 3-fold increase in the amount of αMHC mRNA expression. Increases in the expression of the early cardiomyocyte-associated gene GATA-4 were also detected. In contrast, the endoderm-associated gene HNF3b is not specifically induced under these conditions. The effect on α-MHC and GATA-4 was selective, in comparison with the endoderm-associated gene HNF3b, which increased using any growth factor combination, but not with 5-aza-deoxy-cytidine.

These results demonstrate that factors within Groups I and II enhance the proportion of cells bearing characteristic features of cardiomyocytes.

Example 8

Culturing in a Medium Containing Enrichment Agents

The H9 line of hES cells were differentiated by forming embryoid bodies in suspension for 5 days, and then further differentiating on Matrigel® coated plates for 12 days in differentiation medium. The cells were dissociated using a solution containing 200 U/mL Collagenase II (Worthington), 0.2% trypsin (Irvine Scientific) and 0.02% glucose in PBS. They were plated onto Matrigel® coated plates in differentiation medium, and cultured for a further 14 days.

The cells were then switched to "CCT" medium containing $10^{-7}$ M insulin (Sigma), 0.2% bovine albumin (Sigma), 5 mM creatine (Sigma), 2 mM carnitine (Sigma), and 5 mM taurine (Sigma) in Gibco® medium 199. See Volz et al, J. Mol. Cell Cardiol. 23:161, 1991; and Li et al., J. Tiss. Cult. Meth. 15:147, 1993. For comparison, control cultures were maintained in standard differentiation medium containing 20% FBS.

FIG. 9 shows the number of beating areas after switching to CCT medium (separate lines show observations made for individual wells followed separately during the course of the study). Cells grown in CCT medium showed an increase in the number of beating areas after 7 to 14 days. This shows that the agents creatine, carnitine, and taurine act separately or in combination to enrich the proportion of cardiomyocyte lineage cells in the culture.

Example 9

Four-Phase Centrifugation Separation Method

Cardiomyocytes were generated from hES cells of the H7 line by forming embryoid bodies for 4 days, and then proliferating on gelatin-coated plates for 17 days (5-aza-deoxy-cytidine and growth factors were not used). The cells were then dissociated using collagenase B, resuspended in differentiation medium, and allowed to settle. The cell suspension was then layered onto a discontinuous gradient of Percoll™, and centrifuged at 1500 g for 30 min. Four fractions were collected: I. The upper interface; II. The 40.5% layer; III. The lower interface; IV. The 58.5% layer. The cells were washed and resuspended in differentiation medium. Cells for immunostaining were seeded into chamber slides at $10^4$ cells per well, cultured for 2 or 7, and then fixed and stained.

Results are shown in Table 3. Percentage of MHC positive cells was determined by counting cells in 30 images from triplicate wells for each fraction and presented as mean±standard deviation of cells from 3 wells.

TABLE 3

Percoll ™ Separation

| Fraction | Cell Count | Beating Cells | % staining for MHC | |
|---|---|---|---|---|
| | | | Day 2 | Day 7 |
| Before separation | | + | 17 ± 4.4% | 15 ± 4% |
| I | $9.0 \times 10^6$ | ± | 2.6 ± 0.5% | 2.5 ± 3.0% |
| II | $1.6 \times 10^6$ | + | 4.5 ± 1.5% | 2.4 ± 0.9% |
| III | $4.0 \times 10^6$ | ++ | 35.7 ± 2.7% | 28.3 ± 9.4% |
| IV | $1.3 \times 10^6$ | +++ | 69. ± 5.0% | 52.2 ± 14.5% |

Beating cells were observed in all fractions, but Fractions III and IV contained the highest percentage.

FIG. 10 shows the results of a similar procedure was carried out with hES cells of the H1 line. The cells were separated using Percoll™ on differentiation day 22. Levels of cardiac MHC detected by real time RT-PCR analysis were significantly higher than cells before separation. The data show that Fractions III and IV have the highest level of MHC expression, as a proportion of total transcription using 18S RNA as a standard.

Phenotype of the cells as determined by indirect immunocytochemistry is shown in Table 4.

TABLE 4

Characteristics of Separated Cell Populations

| Epitope | Cardiomyocyte lineage | Non-cardiac cells |
|---|---|---|
| cTnI | ++ | – |
| cardiac-specific α/β MHC | ++ | – |
| cardiac β MHC | ++ | – |
| sarcomeric MHC | ++ | – |
| N-cadherin | ++ | ± |
| smooth muscle actin | ++ | subset |
| myogenin | – | – |
| α-fetoprotein | – | – |
| β-tubulin III | – | – |
| Ki67 | subset | subset |
| BrdU | subset | subset |
| SSEA-4 | – | – |
| Tra-1-81 | – | – |

Cardiomyocyte populations separated by density gradient centrifugation could be distinguished by staining for cTnI and MHC. Absence of staining for myogenin, α-fetoprotein, or β-tubulin III showed the absence of skeletal muscle, endoderm cell types, and neurons. Lack of staining for SSEA-4 and Tra-1-81 confirms the absence of undifferentiated hES cells.

α-Smooth muscle actin (SMA) is reportedly present in embryonic and fetal cardiomyocytes, but not adult cardiomyocytes (Leor et al., Circulation 97:11332, 1996; Etzion et al., Mol. Cell Cardiol. 33:1321, 2001). Virtually all cTnI-positive cells and a subset of cTnI negative cells obtained in the cardiomyocyte differentiation protocol were positive for SMA, suggesting that they may be at an early stage and capable of proliferation.

Cells in fraction III and IV were replated, cultured for an additional 2 days. 43±4% of the MHC positive cells expressed BrdU, indicating that they were in the S phase of the cell cycle. In other experiments, a subset of cTnI-positive cells were found to express Ki-67. These results show that about 20% or 40% of the cardiomyocytes in the population were undergoing active proliferation.

Example 10

Enrichment of Contracting Cells by Making Cardiac Bodies

This example illustrates the subsequent culturing of cardiomycotye clusters as Cardiac Bodies™ to enrich for cells having characteristics desirable for therapeutic use and other purposes.

Three 225 cm² flasks of undifferentiated hES cells of the H7 line were used to generate embryoid bodies as already described. The EBs from each flask were resuspended in 75 mL of medium and transferred to three low adhesion six well plates (4 mL cell suspension per well), yielding nine plates of EBs in suspension in total. After 24 h in suspension, the cultures were gently triturated to disperse aggregated cluster. The EBs were re-fed after one day in suspension by transferring the newly formed EBs to 50 mL conical tubes (one plate per tube), letting the EBs settle at room temperature without agitation for 10 to 20 min, then removing the medium and replacing with fresh medium (25 mL per tube).

The EBs were returned to their original low attachment plates and maintained in suspension in 20% FBS containing medium for 3 additional days, then transferred to a total of three gelatin-coated 225 cm² tissue culture flasks. Two days after transfer to the gelatin coated flasks, the medium was removed and each flask was re-fed with 75 mL 20% FBS containing medium. Similar re-feedings occurred on day 8, 11, 13, 15, and 18. On day 20, the differentiated cultures were dissociated with Blendzyme™ and fractionated on discontinuous Percoll™ gradients as before. Fraction IV (the highest density fraction) was recovered and counted, yielding ~$3.7 \times 10^6$ single cells and small clusters.

The Fraction IV cells were resuspended in ~6.5 mL of 20% FBS containing medium, transferred to a 15 mL conical tube, and allowed to settle at room temperature without agitation for 10 min. The medium (containing $2.8 \times 10^6$ cells, which is most of the single cells) was removed and replaced with fresh medium. The cell suspension was transferred to a single low attachment six well plate (~4 mL of cell suspension per well). The CBs were re-fed in a similar manner (transfer to 50 mL tube, settling for 10 min, medium removal and replacement) every 48 h.

FIG. 11 shows the expression of the sarcomeric genes αMHC and cardiac troponin I as measured by real-time PCR (Taqman™). Relative to the expression after 20 days of culture on gelatin, separating the cells by Percoll™ increased expression by 2-5 fold in Fraction IV cells. Removing the single cells and collecting clusters increased expression to 5-20 fold. After 8 days of culturing the cells as cardiac bodies, the expression was 100- to 500-fold higher than the unseparated cells.

FIG. 12 shows the expression of cTnI measured in cardiac bodies formed from each of the four Percoll™ fractions. Undifferentiated hES cells are used as a negative control. Cardiac bodies could be formed from each of the fractions, but expression of cTnI was especially elevated in Fraction IV cells.

When CBs are replated onto gelatin or Matrigel®, the clusters adhere, flatten, and produce large patches of spontaneously contracting cells. For use in animal testing, the cardiac bodies may be implanted directly, or dispersed into suspensions of single cells.

Example 11

Comparison of Culture Conditions

In this example, the cardiomyocyte differentiation culture was conducted for different periods before Percoll™ separation and cardiac body formation.

Seven 225 cm² flasks of undifferentiated hES cells were used to generate EBs, yielding 21 plates of EBs in suspension in total. As before, the EBs were cultured in 20% fetal bovine serum, plated onto gelatin on day 4, and refed with fresh medium every 2 or 3 days thereafter. On day 12, four flasks of differentiated cells were separated by density gradient centrifugation as before, and on day 20, the remaining 3 flasks were processed. Clustered cells in each of the four Percoll™ fractions were separated, and grown as cardiac bodies. The clusters were separated and fed again at days 2, 5, and 6. On day 7, they were harvested and viewed under the microscope.

FIG. 13 shows a field of cardiac bodies made from Fraction IV cells (bar=300 μm). The clusters marked by the arrows were undergoing spontaneous contractions.

FIG. 14 shows the quantitative data obtained by counting the contracting clusters in each preparation. Fraction IV showed the highest proportion of spontaneously contracting cells, and was higher when the starting population had been differentiated for 20 days. Using a similar protocol, suspensions have been obtained in which it appeared that virtually all of the larger clusters were beating.

The compositions and procedures provided in the description can be effectively modified by those skilled in the art without departing from the spirit of the invention embodied in the claims that follow.

The invention claimed is:

1. A method of generating a cell composition containing cells of cardiomyocyte lineage from human embryonic stem (hES) cells, comprising:
    a) initiating differentiation of the hES cells in suspension culture by forming embryoid bodies in a media comprising serum;
    b) culturing the initiated cells so that they differentiate into cells that undergo spontaneous contraction;
    c) harvesting differentiated cells that demonstrate spontaneous contraction;
    d) separating the harvested cells into fractions based on density wherein the cells are present in a fraction having a density of about 1.05 g/ml, a fraction having a density of about 1.075 g/ml, a fraction including an upper interface of a gradient comprising a fraction having a density of about 1.05 g/ml, and a fraction having a density of about 1.075 g/ml, and a fraction including a lower interface of a gradient comprising a fraction having a density of about 1.05 g/ml, and a fraction having a density of about 1.075 g/ml; and
    e) isolating the cell fractions containing cells that express cardiac troponin I (cTnI), cardiac troponin T (cTnT), or atrial natriuretic factor (ANF) from an endogenous gene;
    thereby generating a cell composition comprising cardiomyocyte lineage cells.

2. The method of claim 1, wherein the embryoid bodies are plated onto a surface coated with gelatin or extracellular matrix.

3. The method of claim 1, wherein the cells are differentiated in the presence of a nucleotide analog that affects DNA methylation.

4. The method of claim 1, wherein the cells are differentiated in a growth environment comprising activin, an insulin-like growth factor and a member of the TGFIβ family.

5. The method of claim 1, wherein the cells are differentiated in a growth environment containing 20% serum or serum substitute.

6. The method of claim 1, wherein the harvested cells are separated by density centrifugation.

7. The method of claim 1, further comprising culturing the collected cells for at least 1 week in a medium containing a compound capable of forming a high energy phosphate bond, an acyl group carrier molecule, and a cardiomyocyte calcium channel modulator.

8. The method of claim 7, further comprising culturing the collected cells for at least 1 week in a medium containing creatine, carnitine, or taurine.

* * * * *

UNITED STATES PATENT AND TRADEMARK OFFICE
CERTIFICATE OF CORRECTION

PATENT NO. : 7,732,199 B2  Page 1 of 1
APPLICATION NO. : 10/805099
DATED : June 8, 2010
INVENTOR(S) : Joseph D. Gold It is certified that error appears in the above-identified patent and that said Letters Patent is hereby corrected as shown below:

Column 36, line 29, in claim 4, "TGFIβ" should read --TGFβ--.

Signed and Sealed this

Seventh Day of September, 2010

David J. Kappos
*Director of the United States Patent and Trademark Office*